(12) United States Patent
Burrowes et al.

(10) Patent No.: US 9,839,930 B2
(45) Date of Patent: Dec. 12, 2017

(54) FLUSHING DISPENSERS FOR DELIVERING A CONSISTENT CONSUMER EXPERIENCE

(71) Applicants: Lee Burrowes, Horsell (GB); Neil Charles Dring, Medmenham (GB); Elaine Alice Marie Baxter, Twickenham (GB); Madhuri Jayant Khanolkar, Singapore (SG); Julien Claude Plos, London (GB); Alastair Robert Edward MacGregor, Egham (GB); Jiten Odhavji Dihora, Liberty Township, OH (US); Adam Gaszton Horvath, West Drayton (GB)

(72) Inventors: Lee Burrowes, Horsell (GB); Neil Charles Dring, Medmenham (GB); Elaine Alice Marie Baxter, Twickenham (GB); Madhuri Jayant Khanolkar, Singapore (SG); Julien Claude Plos, London (GB); Alastair Robert Edward MacGregor, Egham (GB); Jiten Odhavji Dihora, Liberty Township, OH (US); Adam Gaszton Horvath, West Drayton (GB)

(73) Assignee: The Procter & Gamble Company, Cincinnati, OH (US)

( * ) Notice: Subject to any disclaimer, the term of this patent is extended or adjusted under 35 U.S.C. 154(b) by 188 days.

(21) Appl. No.: 14/734,429

(22) Filed: Jun. 9, 2015

(65) Prior Publication Data

US 2016/0361732 A1 Dec. 15, 2016

(51) Int. Cl.
*B05B 11/00* (2006.01)
*B05B 1/34* (2006.01)
(Continued)

(52) U.S. Cl.
CPC .......... *B05B 11/3084* (2013.01); *A61L 9/012* (2013.01); *A61L 9/14* (2013.01);
(Continued)

(58) Field of Classification Search
CPC ............. B05B 11/3081; B05B 11/3083; B05B 11/3084; B05B 15/02; B05B 1/341;
(Continued)

(56) References Cited

U.S. PATENT DOCUMENTS

| 2,800,458 A | 6/1953 | Green |
| 2,730,456 A | 1/1956 | Green et al. |

(Continued)

FOREIGN PATENT DOCUMENTS

| CA | 2735761 | 1/2012 |
| CN | 201537558 | 8/2010 |

(Continued)

OTHER PUBLICATIONS

U.S. Appl. No. 14/734,151, filed Jun. 9, 2015, Dring, et al.
(Continued)

*Primary Examiner* — Arthur O Hall
*Assistant Examiner* — Alexander Valvis
(74) *Attorney, Agent, or Firm* — Betty J. Zea

(57) ABSTRACT

A process for flushing a dispenser that dispenses liquids, especially perfumes, containing microcapsules. The dispenser has a first reservoir for a first composition containing microcapsules and a second reservoir for a second composition containing a volatile solvent. The dispenser also has a swirl chamber and a premix chamber. The process simultaneously pumps the first and second compositions into the premix chamber and then into the swirl chamber. The pumping of the first composition is halted while the pumping of the second composition continues, and this provides
(Continued)

an extra volume of the volatile solvent, which flushes the dispenser to prevent clogging by the microcapsules.

1 Claim, 21 Drawing Sheets

(51) Int. Cl.
  *B05B 15/02* (2006.01)
  *A61L 9/14* (2006.01)
  *A61L 9/012* (2006.01)
(52) U.S. Cl.
  CPC .......... *B05B 1/341* (2013.01); *B05B 11/3081* (2013.01); *B05B 11/3083* (2013.01); *B05B 15/02* (2013.01)
(58) Field of Classification Search
  CPC .......... C11D 3/50; C11D 3/502; C11D 3/505; C11D 3/507; A61L 9/01; A61L 9/012; A61L 9/14
  See application file for complete search history.

(56) References Cited

U.S. PATENT DOCUMENTS

| | | | |
|---|---|---|---|
| 2,800,457 | A | 7/1957 | Green et al. |
| 4,552,811 | A | 11/1985 | Brown et al. |
| 5,152,431 | A | 10/1992 | Gardner et al. |
| 5,169,029 | A * | 12/1992 | Behar ................ B05B 11/3084 128/200.23 |
| 5,398,846 | A | 3/1995 | Corba et al. |
| 5,402,916 | A | 4/1995 | Nottingham et al. |
| 5,482,188 | A | 1/1996 | Lina |
| 5,535,950 | A | 7/1996 | Barriac et al. |
| 5,803,318 | A | 9/1998 | Lina |
| 5,826,048 | A | 10/1998 | Dempsey et al. |
| 5,836,479 | A | 11/1998 | Klima et al. |
| 5,967,372 | A | 10/1999 | Favre |
| 5,971,210 | A | 10/1999 | Brugger |
| 6,454,315 | B1 | 9/2002 | Brozell |
| 6,592,990 | B2 | 7/2003 | Schwantes |
| 7,335,631 | B2 | 2/2008 | McDermott et al. |
| 7,819,342 | B2 * | 10/2010 | Spallek ............. A61M 15/0065 222/137 |
| 8,329,154 | B2 * | 12/2012 | Uchiyama ............. A01N 25/28 424/76.2 |
| 9,102,898 | B2 | 8/2015 | Barone |
| 9,364,838 | B2 | 6/2016 | Parmentier |
| 2003/0215417 | A1 | 11/2003 | Ichiyama et al. |
| 2005/0092778 | A1 | 5/2005 | Bistolfi |
| 2005/0113282 | A1 | 5/2005 | Parekh et al. |
| 2005/0150905 | A1 | 7/2005 | Van Der Heijden et al. |
| 2005/0226900 | A1 | 10/2005 | Brooks et al. |
| 2006/0102656 | A1 | 5/2006 | Troost et al. |
| 2006/0205617 | A1 | 9/2006 | Holzner et al. |
| 2006/0258768 | A1 | 11/2006 | Nara et al. |
| 2010/0108779 | A1 * | 5/2010 | Filsouf ................ B05B 11/0054 239/61 |
| 2011/0268802 | A1 * | 11/2011 | Dihora .................... A61K 8/11 424/489 |
| 2012/0279990 | A1 | 11/2012 | Werner et al. |
| 2014/0178442 | A1 | 6/2014 | Li et al. |
| 2014/0326753 | A1 | 11/2014 | Turner |
| 2015/0071976 | A1 | 3/2015 | Dihora et al. |

FOREIGN PATENT DOCUMENTS

| | | |
|---|---|---|
| EP | 0676339 | 10/1995 |
| EP | 1184071 | 3/2002 |
| EP | 1359212 A1 | 11/2003 |
| EP | 1176945 B1 | 3/2004 |
| FR | 1408299 | 8/1965 |
| GB | 1182520 | 2/1970 |
| JP | 4464803 | 5/2010 |
| WO | WO 2015/031418 A1 | 3/2015 |

OTHER PUBLICATIONS

U.S. Appl. No. 14/734,180, filed Jun. 9, 2015, Dring, et al.
U.S. Appl. No. 14/734,199, filed Jun. 9, 2015, Dring, et al.
U.S. Appl. No. 14/734,234, filed Jun. 9, 2015, Burrowes, et al.
U.S. Appl. No. 14/734,348, filed Jun. 9, 2015, Burrowes, et al.
U.S. Appl. No. 14/734,462, filed Jun. 9, 2015, Burrowes, et al.
U.S. Appl. No. 14/734,512, filed Jun. 9, 2015, Burrowes, et al.
U.S. Appl. No. 14/734,588, filed Jun. 9, 2015, Burrowes, et al.
U.S. Appl. No. 14/734,673, filed Jun. 9, 2015, Burrowes, et al.
Patchan, et al., Liquid-Filled Metal Microcapsules, ACS Appl. Mater. Interfaces, vol. 4, pp. 2406-2412, 2012.
PCT International Search Report dated Sep. 24, 2015—11 pages.
PCT International Search Report dated Sep. 21, 2015—11 pages.
PCT International Search Report dated Sep. 21, 2015—10 pages.
PCT International Search Report dated Nov. 4, 2015—14 pages.
PCT International Search Report dated Aug. 19, 2015—9 pages.
PCT International Search Report dated Sep. 16, 2015—8 pages.
PCT International Search Report dated Sep. 15, 2015—9 pages.
All Office Action U.S. Appl. No. 14/734,151.
All Office Action U.S. Appl. No. 14/734,180.
All Office Action U.S. Appl. No. 14/734,199.
All Office Action U.S. Appl. No. 14/734,348.
All Office Action U.S. Appl. No. 14/734,429.
All Office Action U.S. Appl. No. 14/734,462.
All Office Action U.S. Appl. No. 14/734,512.
All Office Action U.S. Appl. No. 14/734,588.
All Office Action U.S. Appl. No. 14/734,673.
Zhang, Z. et al., "Mechanical Strength of Single Microcapsules Determined by a Novel Micromanipulation Technique," J. Microencapsulation, vol. 16, No. 1, pp. 117-124, 1999.
Sun, G. and Zhang, Z., "Mechanical Properties of Melamine-Formaldehyde Microcapsules," J. Microencapsulation, vol. 18, No. 5, pp. 593-602, 2001.

* cited by examiner

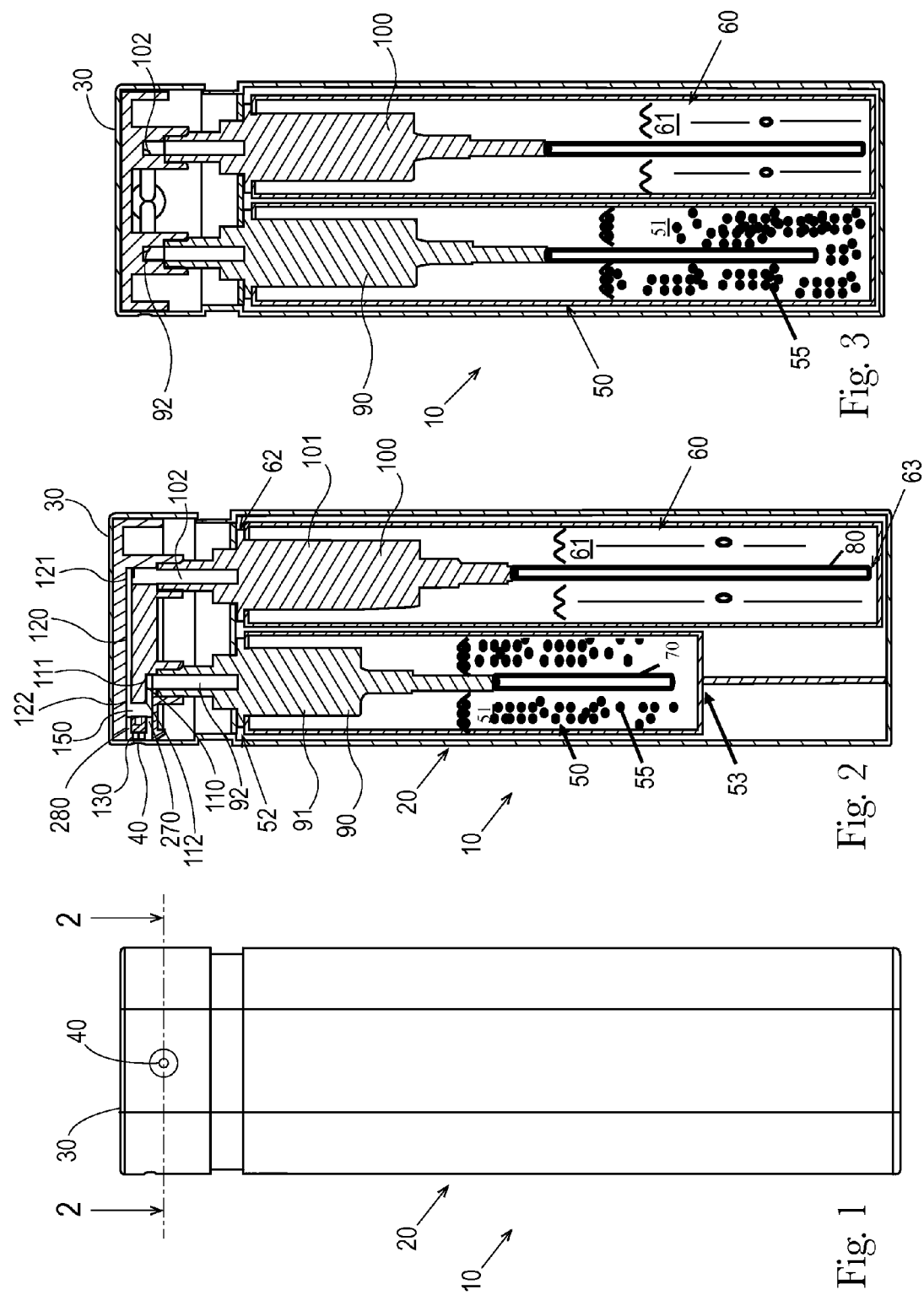

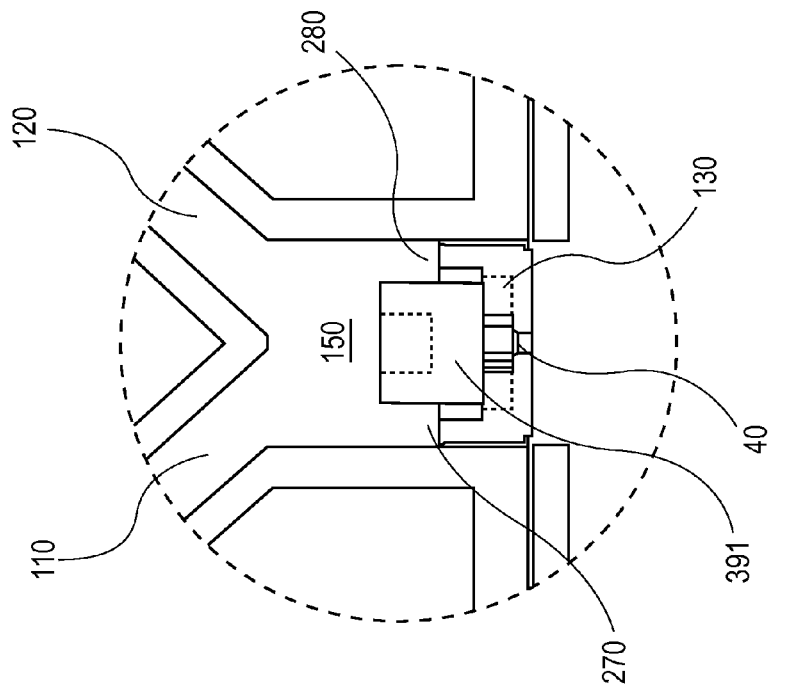
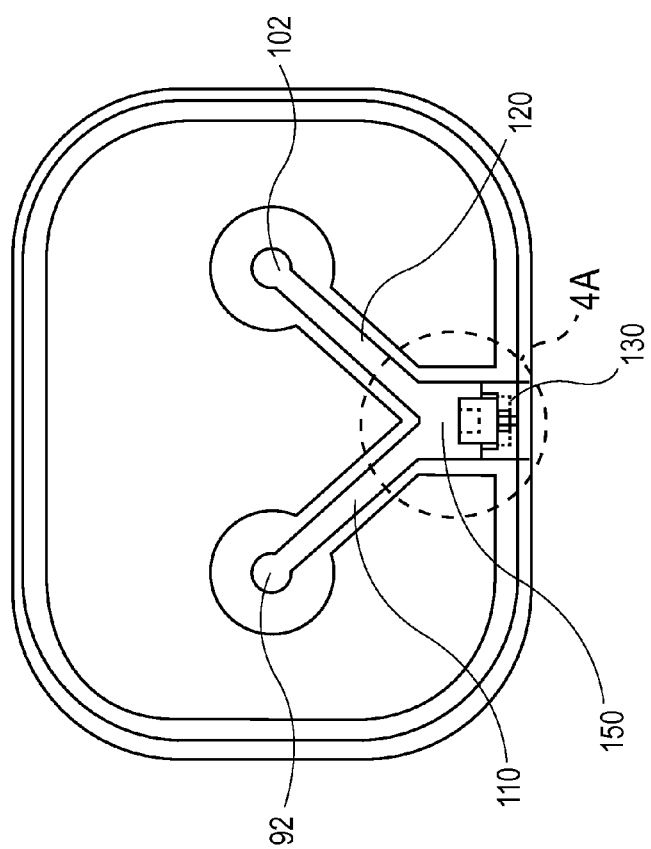
Fig. 4A
Fig. 4

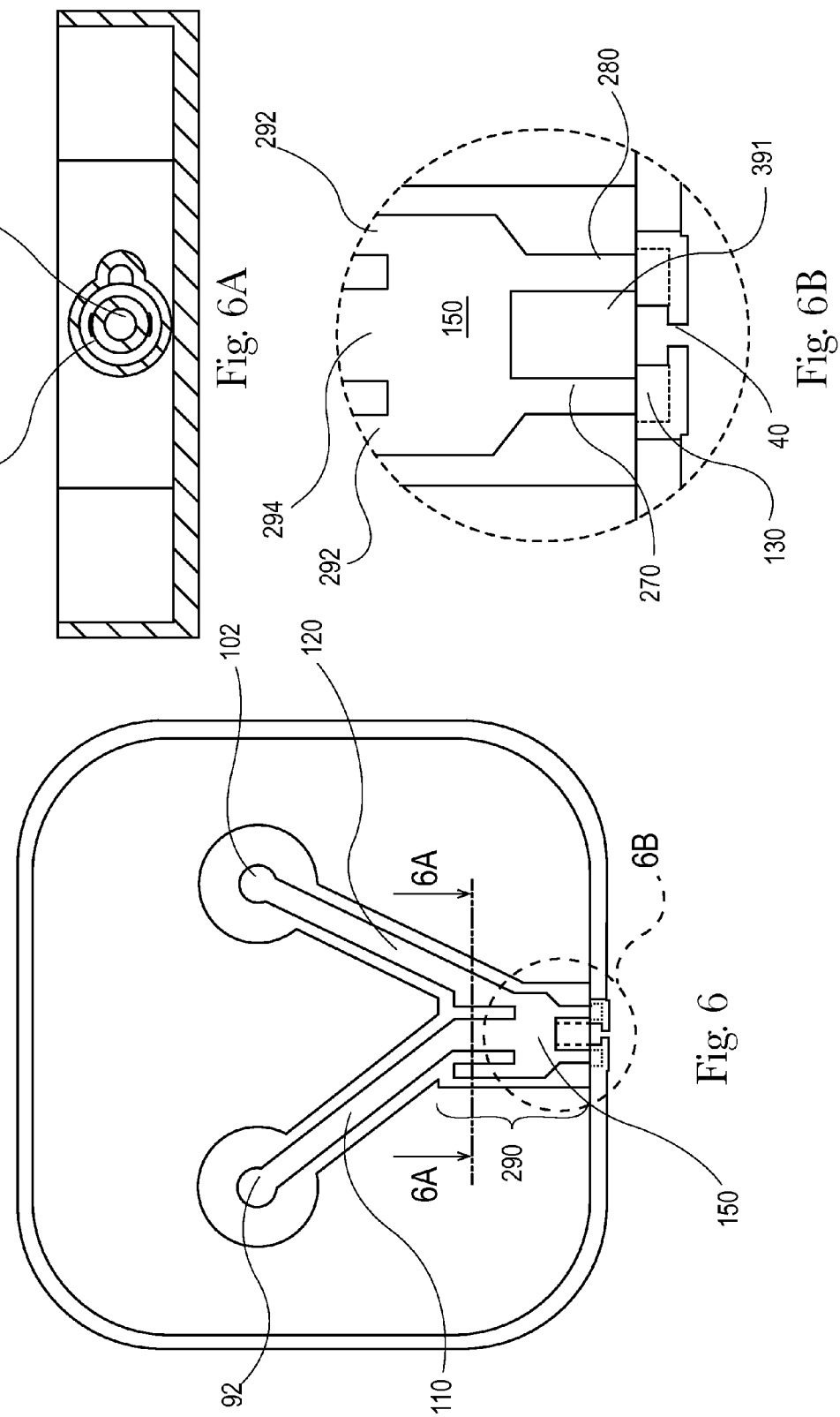

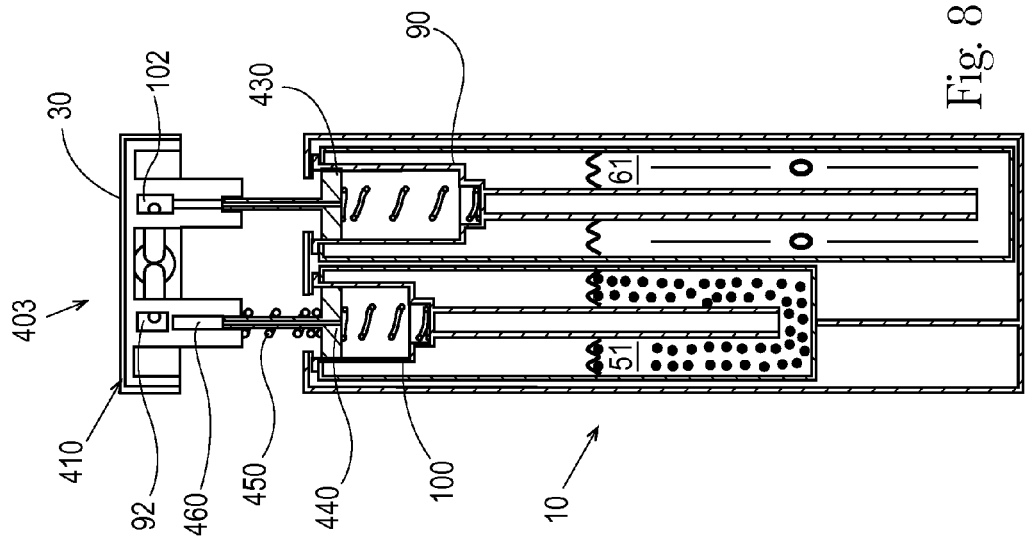
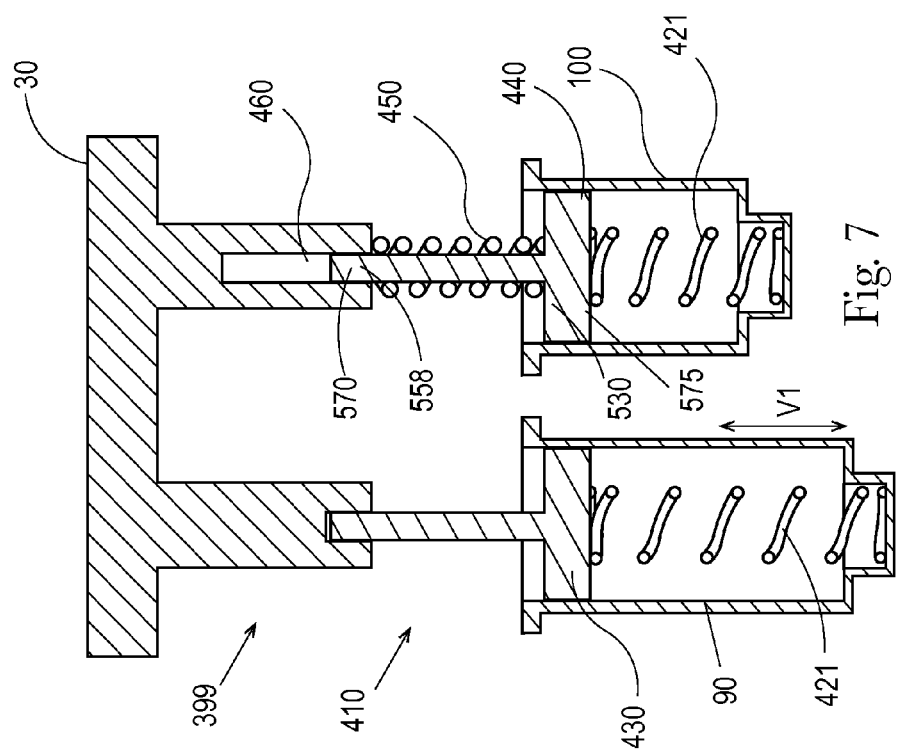

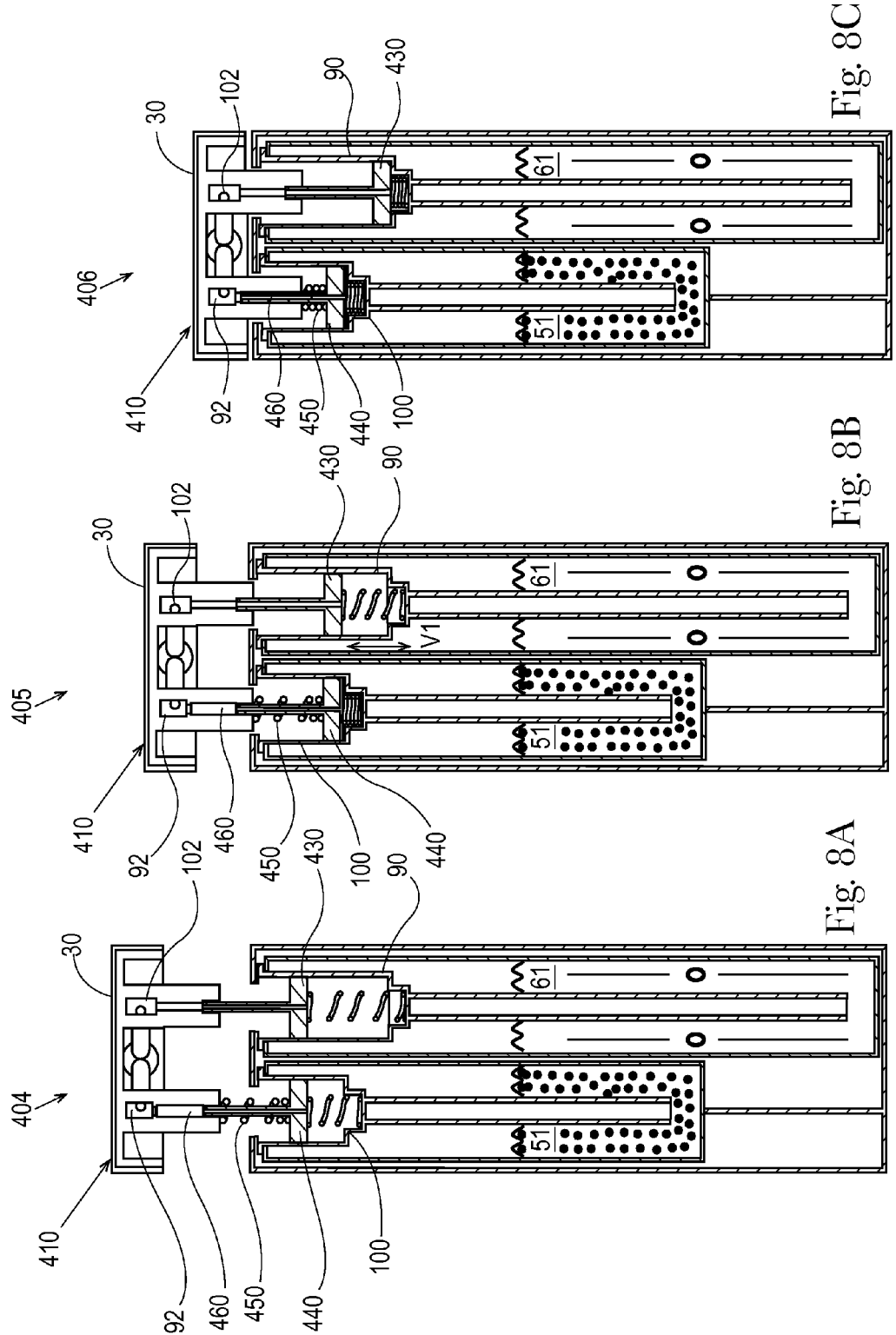

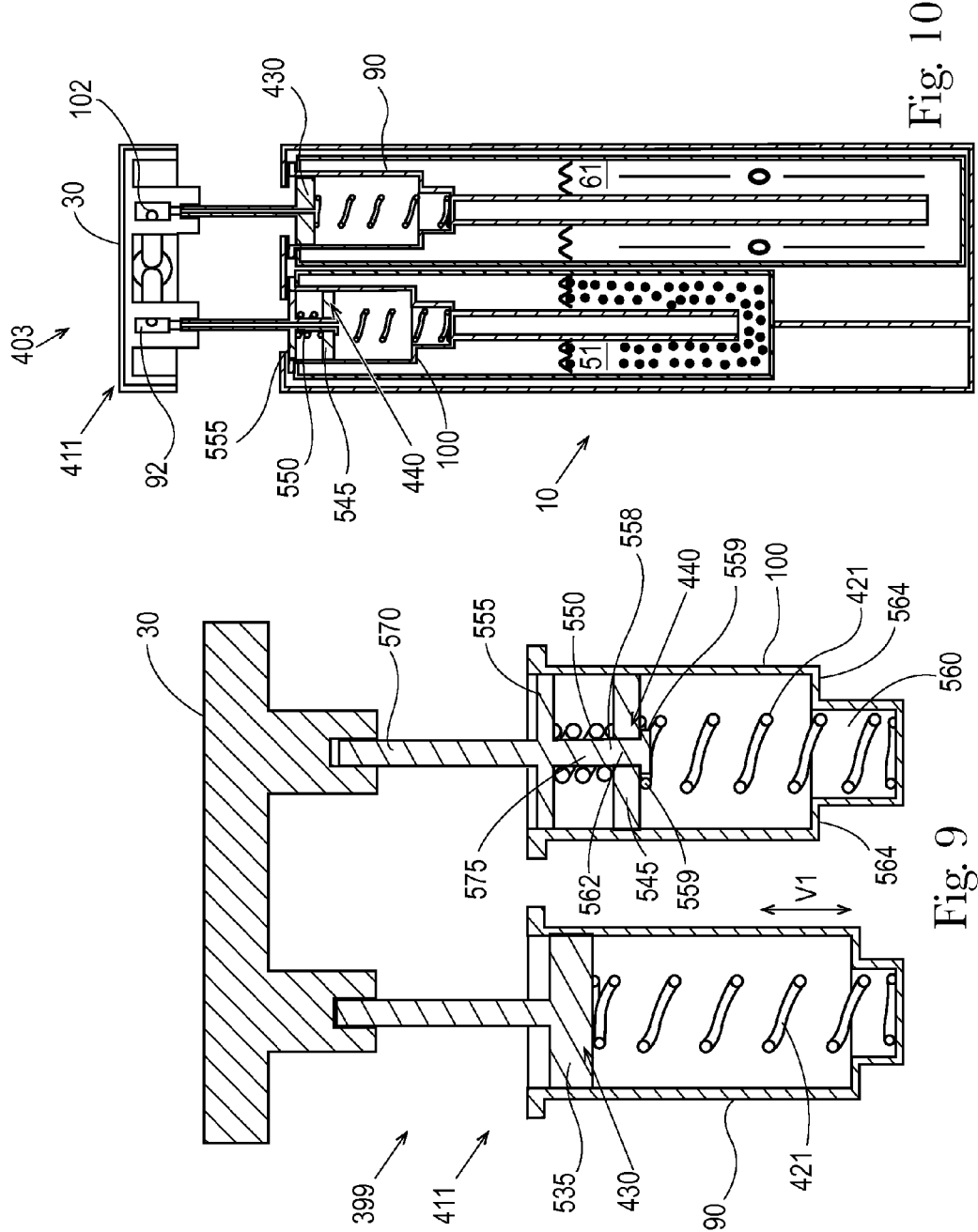

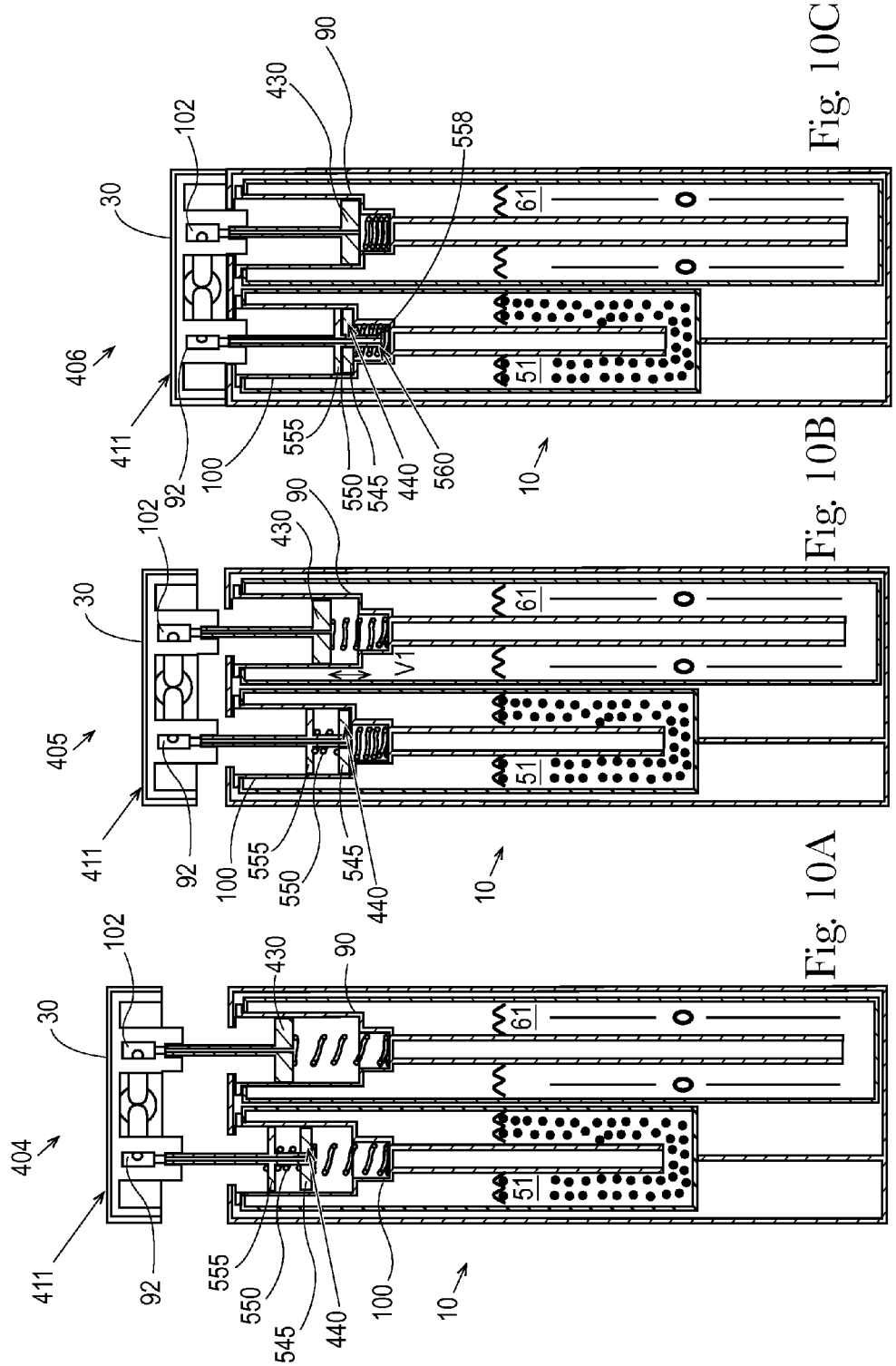

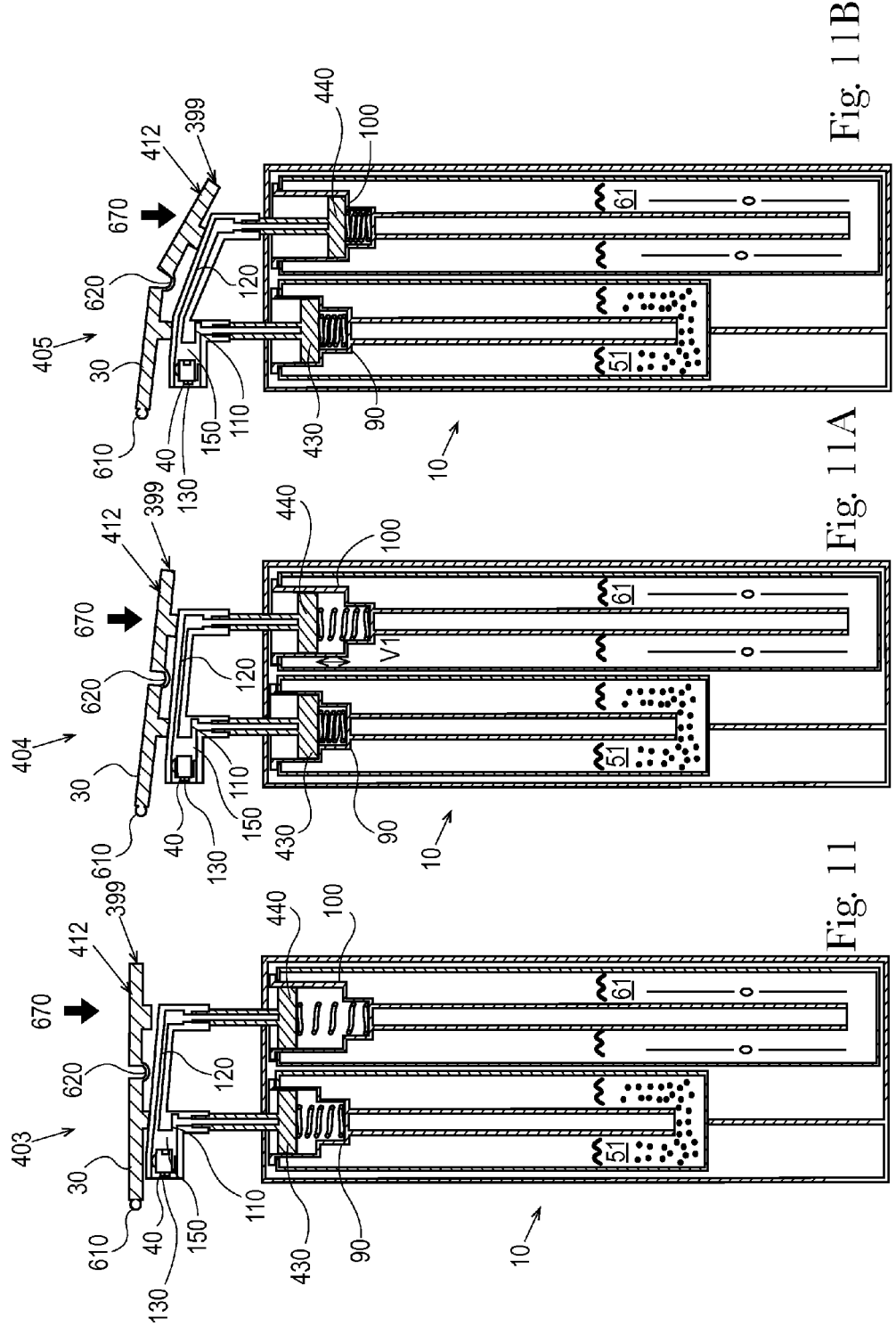

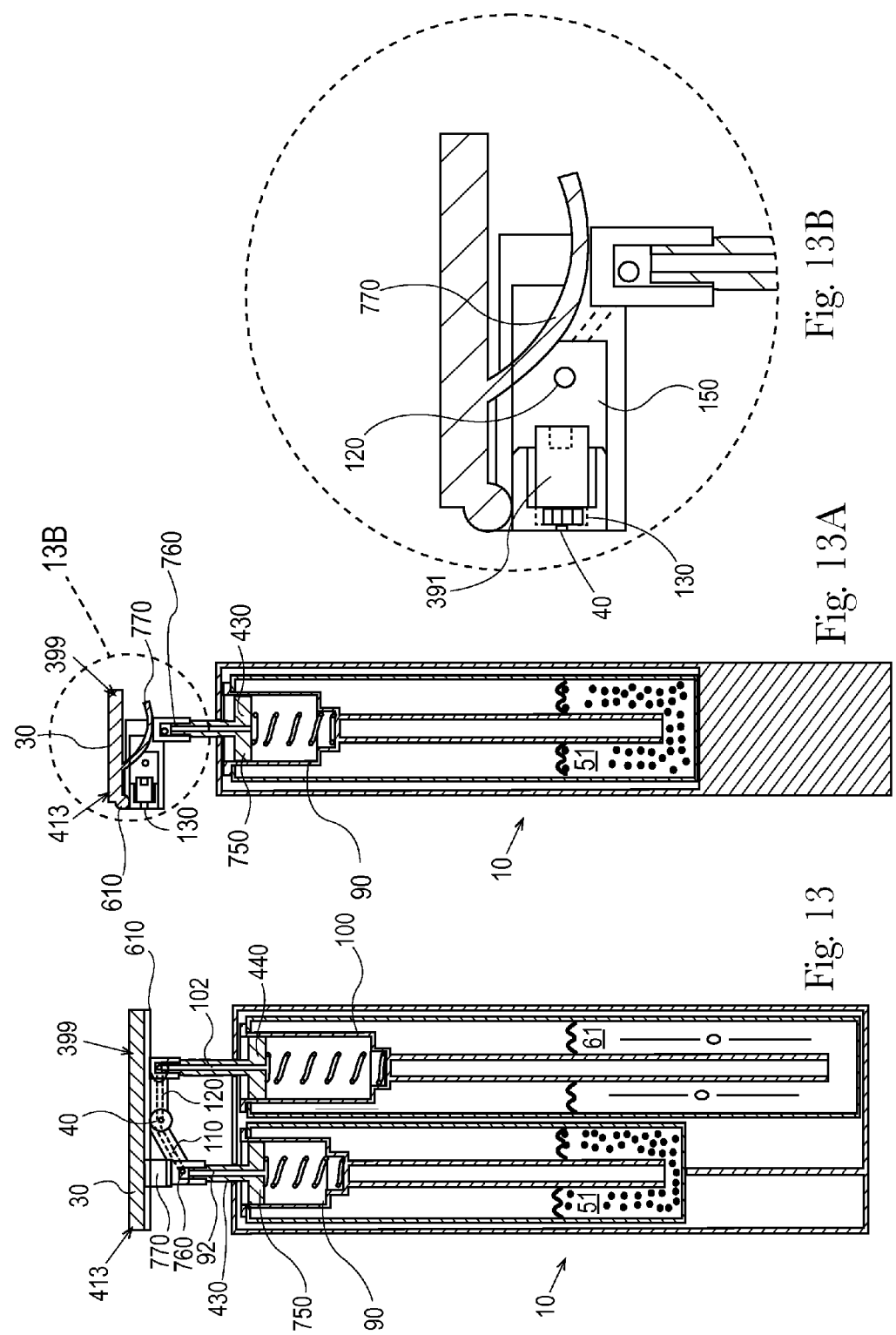

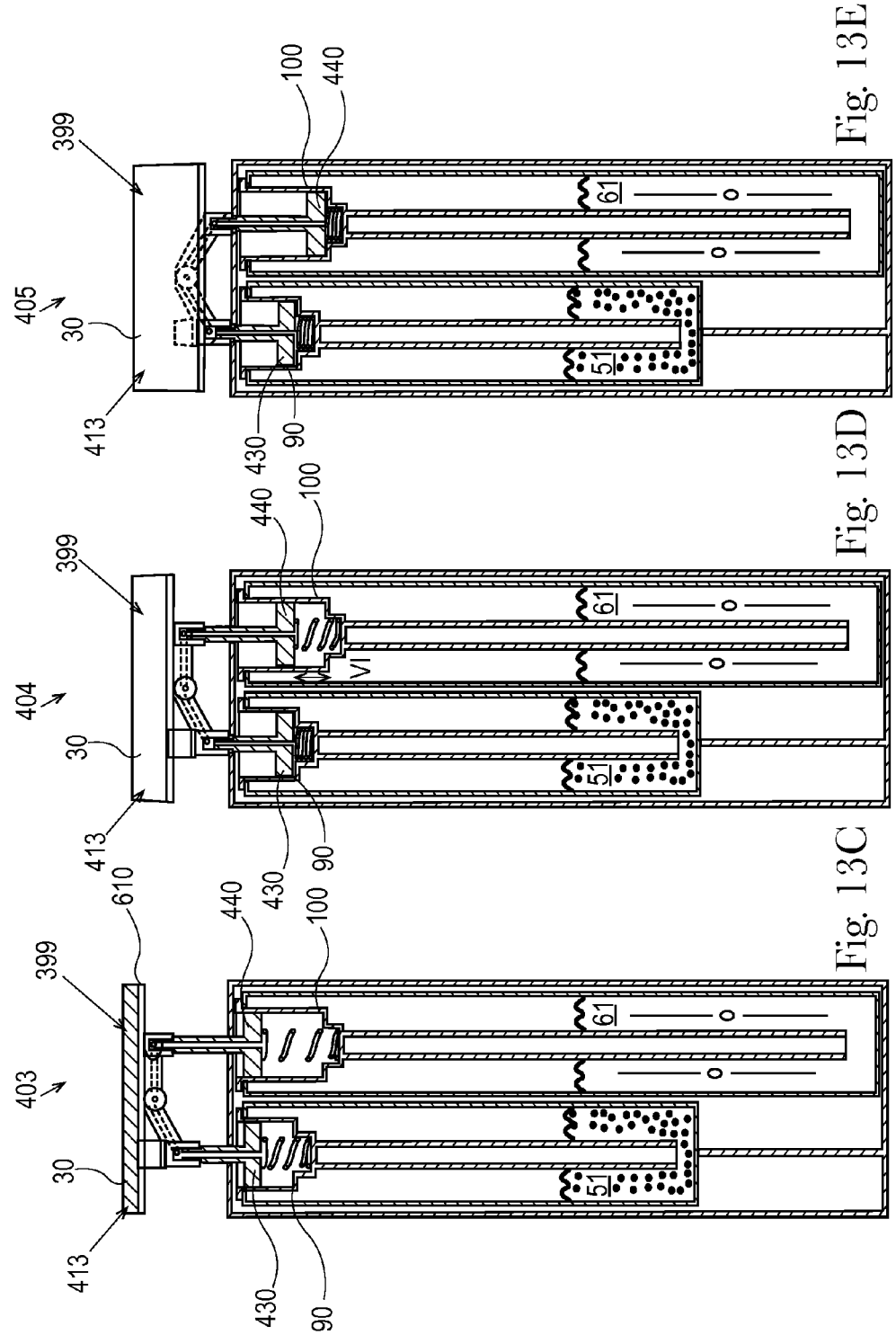

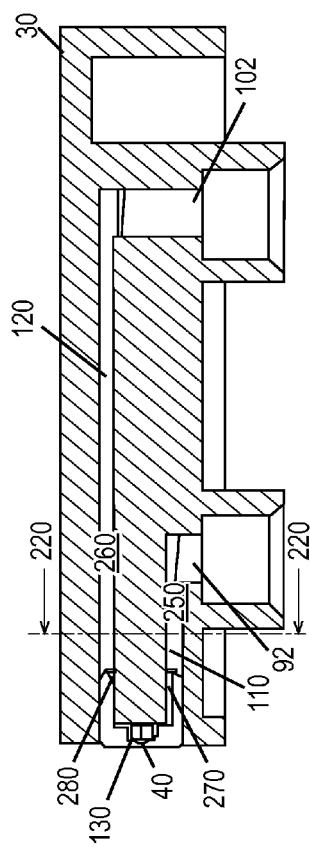
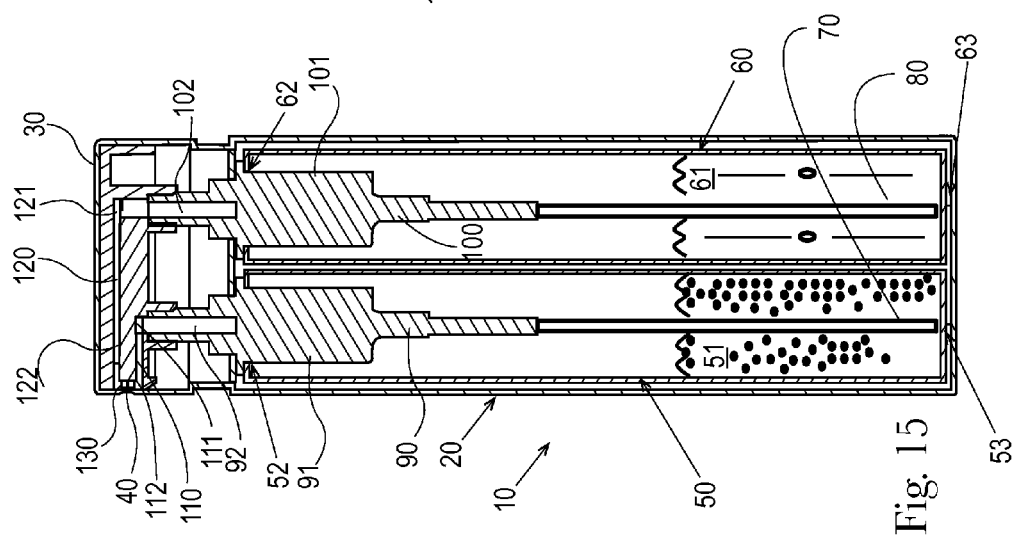

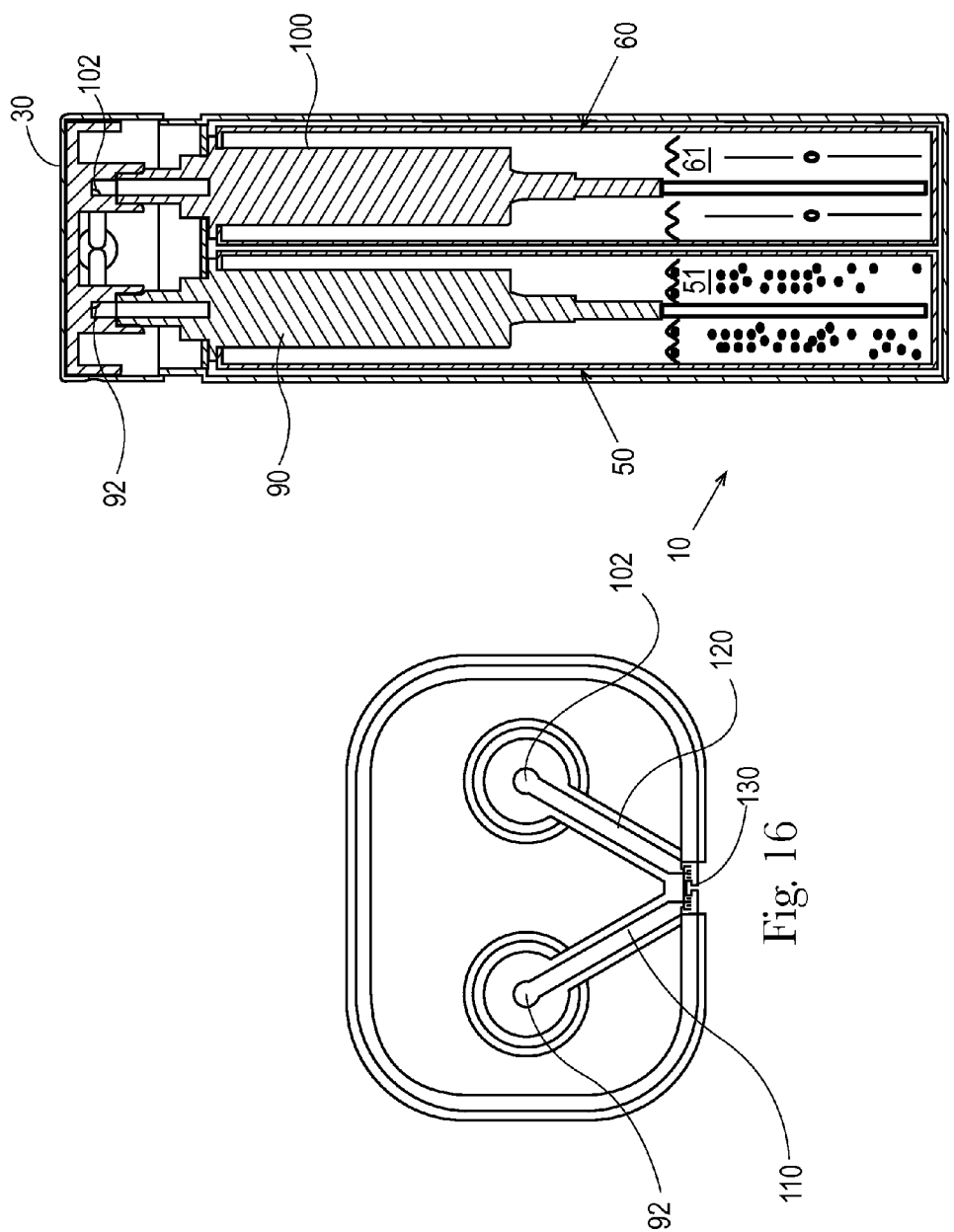

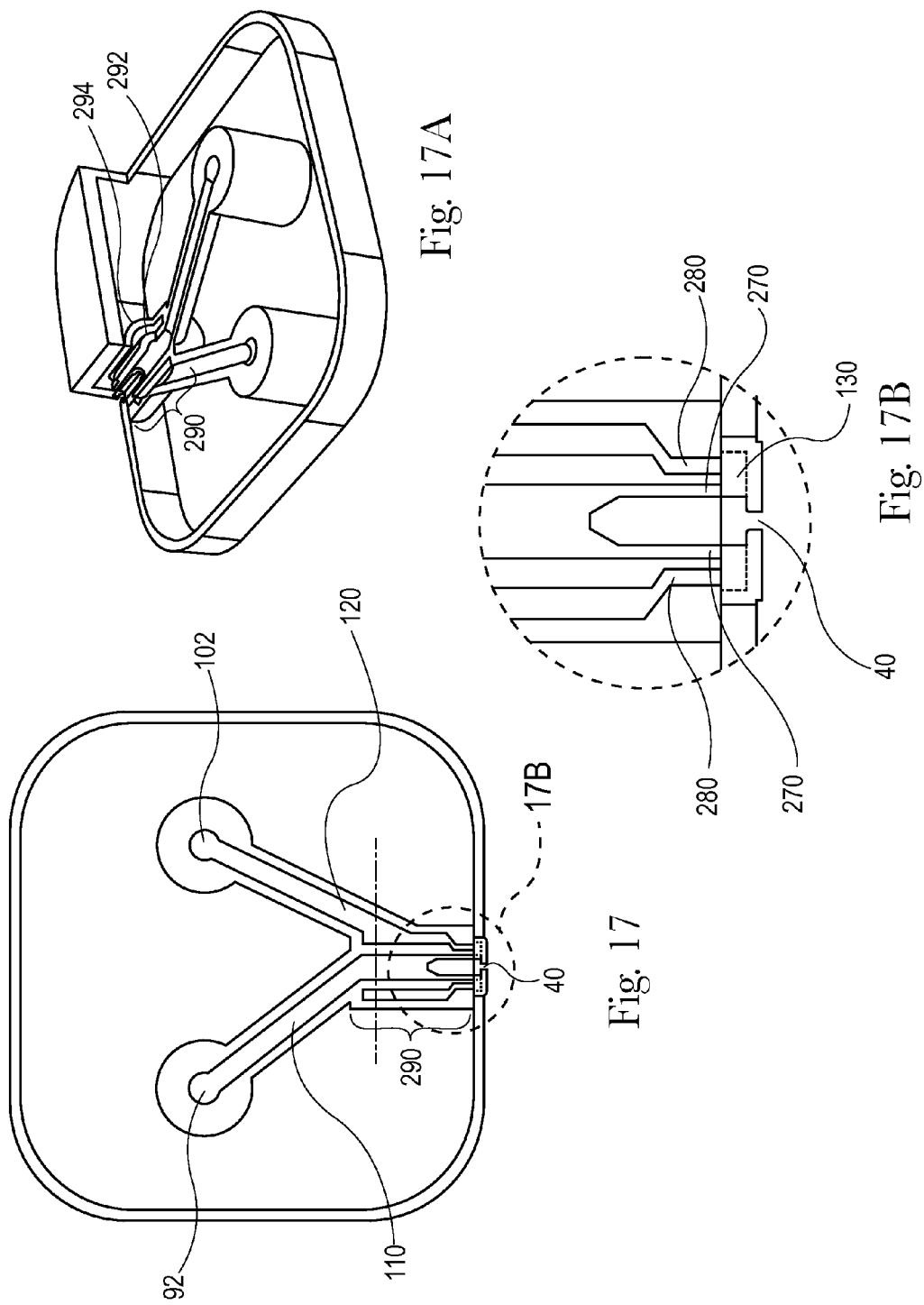

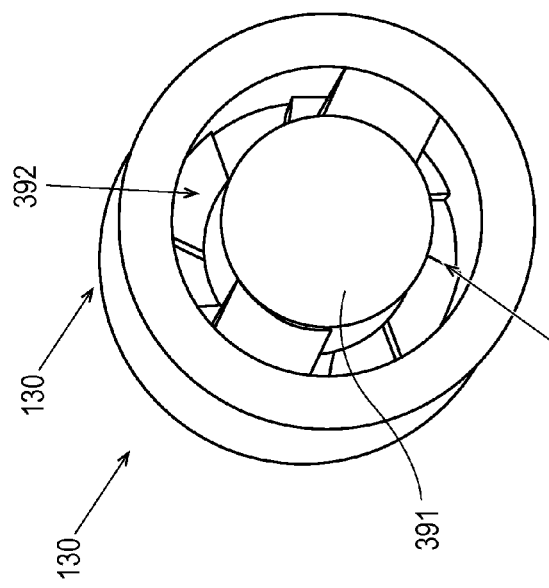
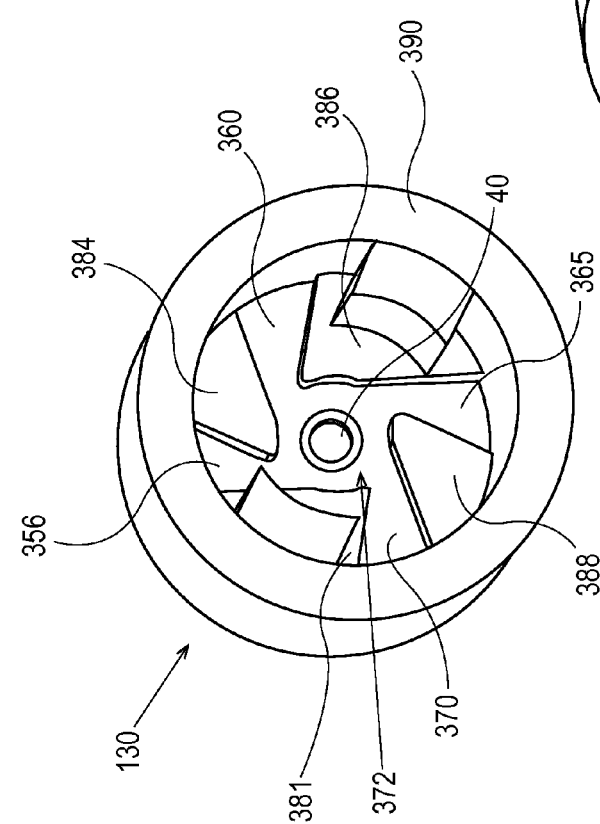
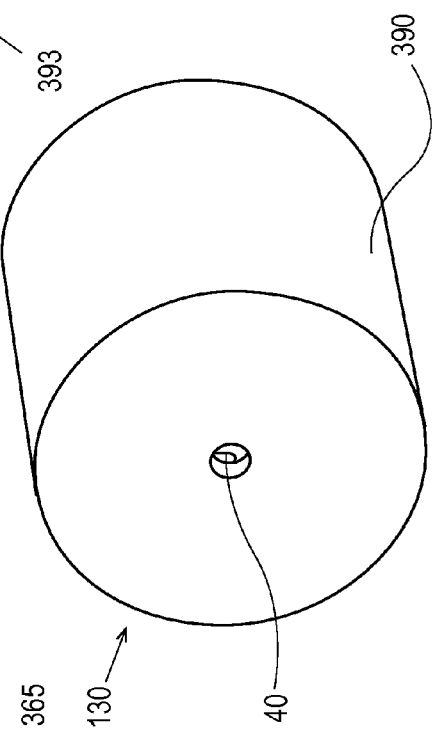
Fig. 18A
Fig. 18B
Fig. 18

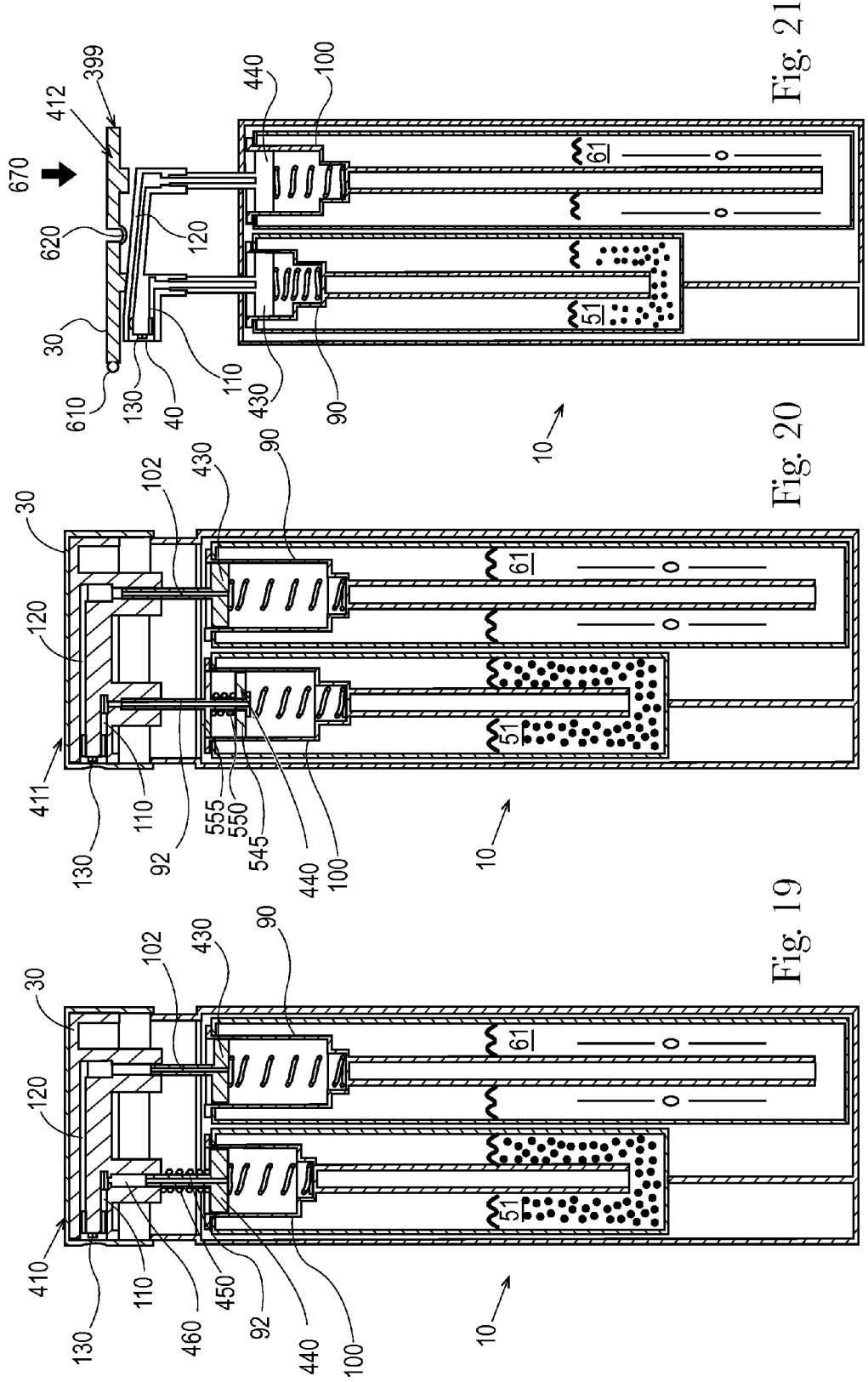

FLUSHING DISPENSERS FOR DELIVERING A CONSISTENT CONSUMER EXPERIENCE

TECHNICAL FIELD

The present disclosure generally relates to methods and assemblies for flushing dispensers.

BACKGROUND

Consumers often desire to deliver pleasant fragrances during and/or after application of a product. Such fragrances often contain perfume oils and/or other odoriferous materials that provide a scent for a limited period of time. It is also not uncommon to include a solvent for solubilizing the perfumes oils and/or other odoriferous materials. At times, such solvents may be incompatible with other ingredients that may provide a benefit to the consumer. While dispensers that contain separate chambers for separating incompatible ingredients may exist, such dispensers may not provide a consistent experience to the consumer or may not be capable of dispensing certain ingredients without damaging and/or clogging the system. Thus, there exists a need for dispensers than can keep some incompatible ingredients separate while delivering a consistent experience to the consumer.

SUMMARY

A process for flushing a dispenser (10), the process comprising: combining the dispenser (10) with an assembly for flushing (399) that provides a first stage and a second stage for pumping a first composition (51) from a first reservoir (50) and a second composition (61) from a second reservoir (60) into at least one of a swirl chamber (130) and premix chamber (150); wherein during the first stage, the first composition (51) and the second composition (61) are substantially simultaneously pumped from the first and second reservoirs (50, 60) and into at least one of a swirl chamber (130) and premix chamber (150); wherein during the second stage, the pumping of one of the first composition (51) and the second composition (61) is halted while the pumping of one of the first composition (51) and the second composition continues, pumping a flushing volume (V1) into at least one of a swirl chamber (130) and premix chamber (15); wherein the first stage occurs before the second stage.

A process for combining a first composition (51) and a second composition (61) to form a mixture and dispensing said mixture through an exit orifice (40), said process comprising: providing a dispenser (10), said dispenser comprising a first reservoir (50) for storing said first composition (51) and a second reservoir (60) for storing said second composition, said dispenser further comprising a first pump (90) in liquid communication with said first reservoir (50) and a second pump (100) in liquid communication with said second reservoir (60), each of said first pump (90) and second pump (100) in liquid communication with a premix chamber (150), said premix chamber (150) in communication with the exit orifice (40), optionally through a swirl chamber (130) and thence through said exit orifice (40); wherein said dispenser further comprises an assembly (399) for operating said first and second pumps (90, 100) substantially simultaneously to provide delivery of a first volume of the first composition (51) and a second volume of the second composition (61) to said premix chamber (150) to form the mixture and to dispense said mixture from said premix chamber (150) via said exit orifice (40); wherein during the formation of said mixed composition, delivery of one of the first and second volume is halted, whereby a final unmixed volume (V1) of the counterpart composition continues to be solely delivered into the premix chamber (150) to flush any residual mixed composition remaining in the premix chamber (150), and optionally the swirl chamber (130), out through the exit orifice (40).

BRIEF DESCRIPTION OF THE DRAWINGS

While the specification concludes with claims, it is believed that the same will be better understood from the following description taken in conjunction with the accompanying drawings in which:

FIG. 1 is a front view of a dispenser;
FIG. 2 is a cross sectional view of the side of a dispenser;
FIG. 3 is a cross sectional view of the front of a dispenser;
FIG. 4 a cross sectional, top view of a dispenser;
FIG. 4A is an enlarged sectional view of an area within FIG. 4;
FIG. 6 a cross sectional, top view of a dispenser;
FIG. 6A is a cross section of an area within FIG. 6;
FIG. 6B is an enlarged sectional view of an area within FIG. 6;
FIG. 7 is a front view of an assembly used in a dispenser;
FIG. 8 is a cross sectional view of the front of a dispenser;
FIG. 8A is a cross sectional view of the front of a dispenser;
FIG. 8B is a cross sectional view of the front of a dispenser;
FIG. 8C is a cross sectional view of the front of a dispenser;
FIG. 9 is a front view of an assembly used in a dispenser;
FIG. 10 is a cross sectional view of the front of a dispenser;
FIG. 10A is a cross sectional view of the front of a dispenser;
FIG. 10B is a cross sectional view of the front of a dispenser;
FIG. 10C is a cross sectional view of the front of a dispenser;
FIG. 11 is a cross sectional view of the side of a dispenser;
FIG. 11A is a cross sectional view of the side of a dispenser;
FIG. 11B is a cross sectional view of the side of a dispenser;
FIG. 13 is a cross sectional view of the back of a dispenser;
FIG. 13A a cross sectional view of the side of a dispenser;
FIG. 13B is an enlarged sectional view of an area within FIG. 13A;
FIG. 13C is a cross sectional view of the back of a dispenser;

FIG. 13D is a cross sectional view of the back of a dispenser;

FIG. 13E is a cross sectional view of the back of a dispenser;

FIG. 15 is a cross sectional view of the side of a dispenser;

FIG. 15A is a partial cross sectional view of a dispenser;

FIG. 16 is a cross sectional, top view of a dispenser;

FIG. 16A is a cross sectional view of the side of a dispenser;

FIG. 17 is a cross sectional, top view of a dispenser;

FIG. 17A is a partial cross sectional view of the top of a dispenser;

FIG. 17B is an enlarged sectional view of an area within FIG. 17;

FIG. 18 is a partial back view of a swirl chamber;

FIG. 18A is a back view of a side of a swirl chamber;

FIG. 18B is a front, perspective view of a swirl chamber;

FIG. 19 is a cross sectional view of the side of a dispenser;

FIG. 20 is a cross sectional view of the side of a dispenser;

FIG. 21 is a cross sectional view of the side of a dispenser; and

DETAILED DESCRIPTION

Figure 3A:
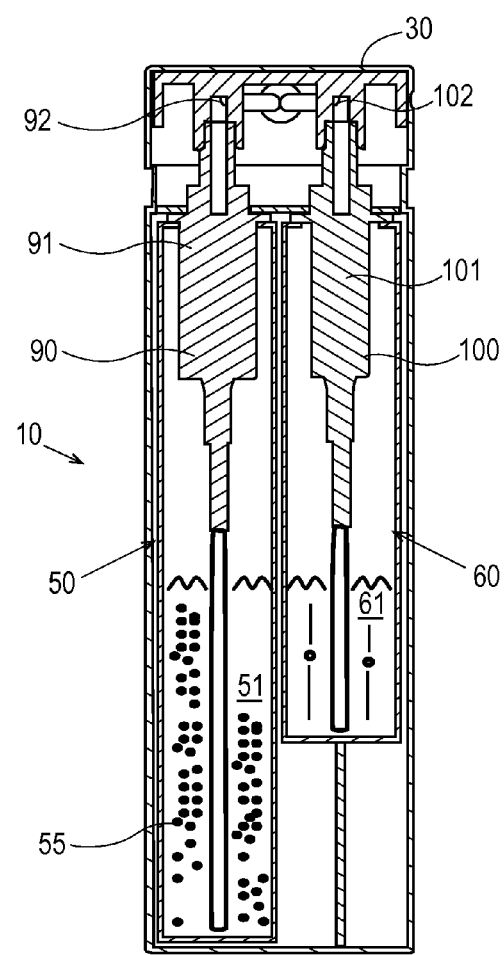
FIG. 3A is a cross sectional view of the front of a dispenser.

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Composition" as used herein, means ingredients suitable for topical application on mammalian keratinous tissue. Such compositions may also be suitable for application to textiles or any other form of clothing including, but not limited to, clothing made from synthetic fibers like nylons and polyesters, and clothing made from acetate, bamboo, cupro, hemp, flannel, jute, lyocell, PVC-polyvinyl chloride, rayon, recycled materials, rubber, soy, Tyvek, cotton, and other natural fibers.

"Exit orifice" herein is shown as a passage from the swirl chamber to the external environment.

"Free of" means that the stated ingredient has not been added to the composition. However, the stated ingredient may incidentally form as a byproduct or a reaction product of the other components of the composition.

"Flushing" or "Flush" refers to the result that occurs when a dispenser provides for two stages of flow in a dispenser where in the first stage both pumps provide delivery of their respective compositions followed by a second stage where only one pump continues to deliver the composition essentially throughout its piston's operating stroke. A non-limiting example of which includes causing a composition containing a volatile solvent to continue to flow after a composition containing encapsulates or after a mixture of compositions containing a volatile solvent and encapsulates has flowed in the dispenser.

"Nonvolatile" refers to those materials that liquid or solid under ambient conditions and have a measurable vapor pressure at 25° C. These materials typically have a vapor pressure of less than about 0.0000001 mmHg, and an average boiling point typically greater than about 250° C.

"Soluble" means at least about 0.1 g of solute dissolves in 100 ml of solvent at 25° C. and 1 atm of pressure.

"Substantially free of" means an amount of a material that is less than 1%, 0.5%, 0.25%, 0.1%, 0.05%, 0.01%, or 0.001% by weight of a composition.

"Derivatives" as used herein, include but are not limited to, amide, ether, ester, amino, carboxyl, acetyl, and/or alcohol derivatives of a given chemical.

"Skin care actives" as used herein, means compounds that, when applied to the skin, provide a benefit or improvement to the skin. It is to be understood that skin care actives are useful not only for application to skin, but also to hair, nails and other mammalian keratinous tissue.

"Volatile," as used herein, unless otherwise specified, refers to those materials that are liquid or solid under ambient conditions and which have a measurable vapor pressure at 25° C. These materials typically have a vapor pressure of greater than about 0.0000001 mmHg, alternatively from about 0.02 mmHg to about 20 mmHg, and an average boiling point typically less than about 250° C., alternatively less than about 235° C.

Fine fragrances, like colognes and parfums, are often desired by consumers for their ability to deliver pleasant scents. A drawback of such fine fragrances is that, because the fragrances are typically volatile, a consumer may have to reapply the fine fragrance after a short period of time in order to keep the same scent expressed. While consumers may desire a fine fragrance product with a longer duration of noticeability, there appears to be no simple solution for extending the duration of noticeability. Hence many fine fragrance products on the market utilize an age old system including a volatile solvent and fragrance oils, said system often offering a short period of noticeability.

One method to increase the duration of noticeability of a fragrance in a product is to incorporate a controlled-release system into the product. In this regard, microcapsules have been included in certain products like deodorants in order to delay the release of a fragrance into the headspace. However, the stability of microcapsules within a composition may be impacted by the ingredients in the composition. For example, some ingredients may cause the microcapsules to be unable to retain their integrity or the encapsulated fragrance to a certain level of degree over time.

It has been observed that the presence of volatile solvents like ethanol in a composition may seriously impact the ability of a fragrance-loaded microcapsule to release its encapsulated fragrance into the headspace. Surprisingly, it has been discovered that minimizing the contact time between the microcapsules and the volatile solvent (e.g. ethanol) allows the microcapsules to deliver a noticeable benefit to a consumer. This can be accomplished by using a dispenser that has at least two reservoirs, one for storing the volatile solvent and the other for storing the microcapsules and their carrier.

It has also been observed that many known dispensers containing at least two reservoirs may not deliver a consistent noticeable benefit from the microcapsules. For example, some dispensers that have more than one reservoir may prematurely mix the microcapsules with the volatile solvent which may lead to clogging and/or damage to the microcapsules themselves. In this regard, some dispensers that have more than one reservoir may retain a significant amount of a mixture of the two compositions from each reservoir somewhere between the exit orifice and the reservoir such that the next actuation may yield a mixture containing damaged microcapsules. Such residual damaged microcapsules may also promote clogging. For example, some dispensers may retain as much as 100% of the composition to be dispensed, by weight of the dispensed amount, depending on the design, between the exit orifice and the reservoir. Also, some dispensers may apply too much force to the microcapsules during the dispensing process such that a significant amount of the microcapsules prematurely release their contents. Because of the incompatibility of the microcapsule and the volatile solvent, such dispensers may deliver an inconsistent olfactory experience to the consumer.

Another significant problem that may present itself is that the carrier that may be used for the microcapsules may have a high surface tension such that the composition containing the microcapsules is resistant to atomization. For example when the carrier is water, the high surface tension of water (73 dynes/cm at 20° C.) may resist atomization such that a stream is more likely dispensed rather than a spray. The introduction of a suspending agent for the microcapsules may further exacerbate the problem because the suspending agent may increase the viscosity of the composition containing the water and microcapsules, making it less likely said composition can overcome its relatively high surface tension for atomization. It is well known that compositions having a high surface tension and a high viscosity are difficult to atomize without significant pressure generation. If the composition is not dispensed with sufficient atomization, such a dispenser may not be desirable for a high-end product like a fine fragrance.

In this regard, dispensers that mix the two compositions in-flight (i.e. the compositions are kept separate throughout the dispenser and are dispensed via distinct exit orifices, with the angle of exit of each composition leading to a mixing of the two compositions in the air) are unlikely to be useful when the second composition includes a volatile solvent and the first composition includes water as the composition containing water is resistant to atomization. In such a design, it is more than likely that the composition containing the volatile solvent may atomize while the composition containing water will be resistant to atomization; leading to what appears to the user as fine stream within a spray. If such a result occurs, such a dispenser may not be desirable for a high-end product like a fine fragrance.

Dispenser

In order to prevent the buildup of residual damaged microcapsules within a dispenser, the dispensers described herein are customized to allow for a flushing of the components of the mixture in order to remove any residual microcapsules that have come into contact with the volatile solvent. These residual microcapsules may in some cases promote clogging. The residual microcapsules may also leave an unsightly residue at or near the exit orifice that may be undesirable for a fine fragrance product. Without being limited by theory, it is believed that the concentration and type of microcapsule used may in some cases lead to a clogging of the dispenser. To alleviate these problems, a dispenser may be customized to include an assembly for flushing (399). Some non-limiting examples of dispensers are described herein.

Flushing can be achieved by several different designs. However, all of said designs utilize a common process. The process relies on at least two pumps, where both pumps provide delivery of their respective compositions during the first, "productive" stage. Thereafter, while one pump continues to deliver the composition, providing for a flushing volume (V1) to flush the swirl chamber (and potentially other components), the other pump enters a "non-productive" stage wherein essentially no more composition is delivered from that pump. In some examples, the flushing volume (V1) should be enough to flow through the elements of the dispenser exposed to the mixture of the first and second compositions. In some examples, if the volume of the swirl chamber, premix chamber, and the exit orifice is 12 microliters in volume, then the V1 should be equal to or greater than 12 microliters. To ensure the dispenser provides a consistent consumer experience by minimizing the amount of residual mixture left within the dispenser after each actuation event, the volume of V1 should range from about 5 microliters to about 50 microliters when the dispensed volume is from about 30 microliters to about 300 microliters.

It is to be understood that an assembly for flushing (399) may be used in conjunction with a premix chamber (150), as described herein. Alternatively, the assembly for flushing (399) may be used when the compositions are delivered directly to a swirl chamber (130). Alternatively, the assembly for flushing (399) may be used when the compositions are delivered directly to the exit orifice (40).

The dispensers disclosed herein may provide for a consistent consumer experience and a prolonged period of noticeability of a fragrance. The dispensers described herein minimize the contact time between the microcapsules and a volatile solvent (e.g. ethanol), allowing the microcapsules to deliver a noticeable benefit to the user. The dispensers described herein include at least two reservoirs, one for separately storing each of the first and second compositions. The dispensers may also include a swirl chamber for atomizing the two compositions. The first and second compositions exit the dispenser via a common exit orifice. The dispensers may also utilize at least two pumps fitted with pistons, one pump for pumping the first composition and a second pump for pumping the second composition to a common swirl chamber and exit orifice. Each pump pumps each composition into a channel that serves to deliver the composition from the reservoir to at least one of the swirl chamber and exit orifice.

In some examples, the dispensers described herein may mix the two compositions immediately prior to exit by first mixing the compositions within a premix chamber (150). The premix chamber (150) may have a volume sufficient to contain from 1% to 100% of the dispensed amount by volume, alternatively from 1% to 75% of the dispensed amount, alternatively from 2% to 20% of the dispensed amount, alternatively from 4% to 14% of the dispensed amount. In some examples, it may be preferable to limit the volume of the premix chamber in order for the dispenser to yield a consistent consumer experience as such a design will limit the extent of damaged microcapsules sprayed from the dispenser during each actuation event. The following is a non-limiting example: if the total volume of the dispensed mixture is 105 microliters and the dispensed mixture contains about 35 microliters of the first composition and 70 microliters of the second composition, the premix chamber (150) may have a volume sufficient to mix between 5 microliters and 15 microliters of the first and second compositions combined. In some examples, the premix chamber may include one or more baffles (not shown) to create turbulence and improved mixing.

Mixing within the premix chamber (150) as described herein provides several advantages. First, the dispensers herein take advantage of the fact that the mixture of certain volatile solvents like ethanol with water results in a mixture with a lower surface tension than water, increasing the likelihood that the two compositions are appropriately aerosolized. Second, by limiting the duration and extent of the mixing, the microcapsules are less likely to be damaged upon exit. Third, limiting the duration and extent of mixing also minimizes potential clogging. Lastly, the designs herein provide a consistent consumer experience by minimizing the amount of residual mixture left within the dispenser after each actuation event.

The size of the dispenser may be such as to allow it to be handheld. The dispenser may include a first composition stored in a first reservoir and a second composition stored in a second reservoir. The second composition may include a volatile solvent and a first fragrance. The first composition may include a plurality of microcapsules and a carrier (e.g. water). The first composition may further include a suspending agent. The first and second compositions may each further include any other ingredient listed herein unless such an ingredient negatively affects the performance of the microcapsules. Non-limiting examples of other ingredients include a coloring agent included in at least one of the first and second compositions and at least one non-encapsulated fragrance in the second composition. When the first composition comprises microcapsules encapsulating a fragrance, the first composition may further include a non-encapsulated fragrance that may or may not differ from the encapsulated fragrance in chemical make-up. In some examples, the first composition may be substantially free of a material selected from the group consisting of a propellant, ethanol, a detersive surfactant, and combinations thereof; preferably free of a material selected from the group consisting of a propellant, ethanol, a detersive surfactant, and combinations thereof. Non-limiting examples of propellants include compressed air, nitrogen, inert gases, carbon dioxide, gaseous hydrocarbons like propane, n-butane, isobutene, cyclopropane, and mixtures thereof. In some examples, the second composition may be substantially free of a material selected from the group consisting of a propellant, microcapsules, a detersive surfactant, and combinations thereof; preferably free of a material selected from the group consisting of propellant, microcapsules, a detersive surfactant, and combinations thereof.

The dispenser may be configured to dispense a volume ratio of the second composition to the first composition at a ratio of from 10:1 to 1:10, from 5:1 to 1:5, from 3:1 to 1:3, from 2:1 to 1:2, or even 1:1 or 2:1, when the second composition comprises a volatile solvent and the first composition comprises a carrier and a plurality of microcapsules, according to the desires of the formulator. The dispenser may dispense a first dose of the second composition and a second dose of the first composition such that the first dose and the second dose have a combined volume of from 30 microliters to 300 microliters, alternatively from 50 microliters to 140 microliters, alternatively from 70 microliters to 110 microliters.

As shown in FIG. 1, the dispenser 10 may have a housing 20, an actuator 30 and an exit orifice 40. In some non-limiting examples, the exit orifice may have a volume of 0.01 cubic millimeters to 0.20 cubic millimeters, such as when the exit orifice 40 has a volume of 0.03 cubic millimeters. In some examples, the housing 20 may not be necessary; a non-limiting example of which is when the reservoirs 50, 60 are made of glass. When the reservoirs are made of glass, the two reservoirs may be blown from the same piece of molten glass, appearing as a single bottle with two reservoirs. Alternatively, when the reservoirs are made of glass, the two reservoirs may be blown from separate pieces of molten glass, appearing as two bottles, each with a single reservoir, and joined together via a connector. One of ordinary skill in the art will appreciate that many possible designs of the reservoirs are possible without deviating from the teachings herein; a non-limiting example of which is a reservoir within a reservoir.

As shown in FIG. 2, the dispenser 10 may also contain a first reservoir 50 for storing a first composition 51 and a second reservoir 60 for storing a second composition 61. The reservoirs 50, 60 may be of any shape or design. The dispenser may be configured to dispense a non-similar volume ratio (not 1:1) of the first composition 51 to the second composition 61, as shown in FIG. 2. The first reservoir 50 may have an open end 52 and a closed end 53. The second reservoir may have an open end 62 and a closed end 63. The open ends 52, 62 may be used to receive the pump, channel, and/or dip tubes into the reservoirs. The open ends 52, 62 may also be used to supply the reservoirs with the compositions. Once supplied, the open ends 52, 62 may be capped or otherwise sealed to prevent leakage from the reservoirs. In some examples, the first composition 51 may include microcapsules 55. The dispenser may include a first dip tube 70 and a second dip tube 80, although the dip tubes are not necessary if alternative means are provided for airless communication between the reservoir and the pump, a non-limiting example of which is a delaminating bottle. The dispenser may include a first pump 90 (shown as a schematic) in communication with the first dip tube 70. The dispenser may also include a second pump 100 (shown as a schematic) in communication with the second dip tube 80. The dispenser may also be configured to contain a first pump 90 and a second pump 100 with different output volumes. In some non-limiting examples, at least one pump may have an output of 70 microliters and the other pump may have an output of 50 microliters.

As shown in FIG. 2, the first reservoir 50 may be configured to hold a smaller volume than the second reservoir 60 or vice versa when non-similar ratios of the first composition to the second composition are to be dispensed. If dip tubes are included, the first dip tube 70 may also be of a shorter length than the second dip tube 80 or vice versa. The inner workings of the pumps are routine unless otherwise illustrated in the drawings. Such inner workings have been abbreviated and shown as schematic so as to not detract from the teachings herein. Suitable pumps with outputs between 30 microliters to 140 microliter may be obtained from suppliers such as Aptargroup Inc., MeadWeastavo Corp., and Albea. Some examples of suitable pumps are the pre-compression pumps described in WO2012110744, EP0757592, EP0623060. The first pump 90 may have a chamber 91 and the second pump 100 may have a chamber 101. As illustrated in FIG. 2, the first pump 90 and second pump 100 may be configured so that the chambers 91, 101 have different lengths and similar or the same diameters. The pumps as illustrated herein are in some cases magnified to show the inner details and may be smaller in size than they appear as illustrated herein when said pumps are used for a fine fragrance.

As shown in FIG. 2, the dispenser may include a first channel 110 and a second channel 120. In some non-limiting examples, the channels 110, 120 have a volume of 5 millimeters to 15 millimeters, an example of which is when the channels have a volume of 8.4 cubic millimeters. The first channel 110 may have a proximal end 111 and a distal end 112. The second channel 120 may have a proximal end 121 and a distal end 122. The proximal end 111 of the first channel 110 is in communication with the exit tube 92 of the first pump 90. The proximal end 121 of the second channel 120 is in communication with the exit tube 102 of the second pump 100. The first channel 110 may be of a shorter length as compared to the second channel 120. The second channel 120 may be disposed above the first channel 110 as illustrated in FIG. 2 or below the first channel 110. Alternatively, the first channel and second channel may be substantially coplanar (i.e. exist side-by-side). The exit tubes 92, 102 may have similar or different diameters which can provide for similar or different volumes. In some non-limiting examples, the exit tubes have a diameter of 0.05 millimeters to 3 millimeters, an example of which is when one of the exit tubes has a diameter of 1.4 millimeters and the other exit tube has a diameter of 1 millimeter. In some non-limiting examples, the exit tubes 92, 102 may have a volume of from 2 cubic millimeters to 10 cubic millimeters, such as when one exit tube has a volume of 7.70 cubic millimeters and the other exit tube as a volume of 3.93 cubic millimeters.

To minimize clogging such as may occur when a composition contains particulates (e.g. microcapsules) or displays a different viscosity from the other composition, the channels 110, 120 may be configured such that one of the channels has a larger diameter than the other. The channel with the larger diameter may be used to prevent clogging when particulates are contained within a composition.

The distal end 112 of the first channel 110 and the distal end 122 of the second channel 120 serve to deliver the compositions into the premix chamber 150. In some examples, the premix chamber 150 may include inner baffles to facilitate mixing. The dispenser may also include at least one feed to deliver the mixture of the first and second composition from the premix chamber 150 to the swirl chamber 130. The swirl chamber 130 may impart on the first composition 51 and the second composition 61 a swirl motion. In some examples, the dispenser may include a first feed 270 in communication with the swirl chamber 130 and the premix chamber 150, as illustrated in FIG. 2. The dispenser may also include a second feed 280 in communication with the swirl chamber 130 and the premix chamber 150. The first feed 270 may be configured to have a different diameter as compared to the second feed 280. Alternatively, the feeds 270, 280 may have a substantially similar diameter. In some examples, the dispenser may have more than two feeds. The swirl chamber 130 may impart on the first composition 51 and the second composition 61 a swirl motion. The swirl chamber may be configured to deliver certain spray characteristics. For example, the fluid entering the swirl chamber may be provided a swirling or circular motion or other shape of motion within the swirl chamber, the characteristics of the motion being driven by the inward design of the swirl chamber 130. In some instances, the mixing of the two compositions in the premix chamber 150 may lower the surface tension of the compositions, and thereby, improving the level of atomization of the liquids. Incorporation of a swirl chamber 130 may further promote atomization when compositions that vary in surface tension and viscosity are present in the reservoirs. Alternatively, the dispenser 10 may be configured to dispense a volume similar ratio (e.g. 1:1) of the first composition 51 to the second composition 61, as shown in FIG. 3. In some examples, the reservoirs 50 and 60 may be of a similar size. The first pump 90 and the second pump 100 may selected to deliver similar outputs. In some examples, the dispenser may be configured so that the chambers 91, 101 have similar or the same diameters while having the same or similar lengths that allow for the same or similar stroke lengths for the pistons.

In some examples, the dispenser may be configured so that the reservoir supplying the composition containing the microcapsules is delivered via the longer channel when the channels are of different lengths.

Figure 3B:
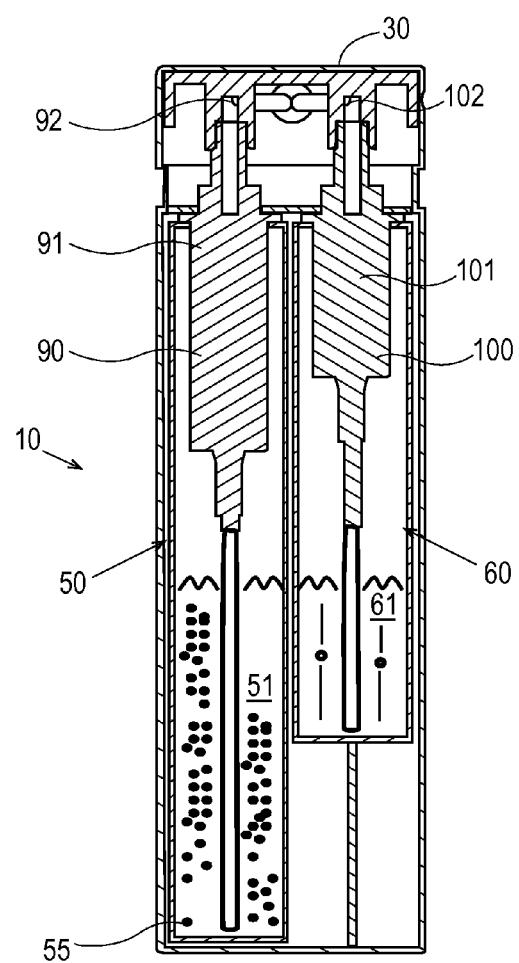
FIG. 3B is a cross sectional view of the front of a dispenser.

Alternatively, the dispenser may be configured to dispense a non-similar volume ratio (not 1:1) of the first composition 51 to the second composition 61, as shown in FIG. 3A. In some examples, the first pump 90 and the second pump 100 may be configured so that the chambers 91 101 have different diameters while having the same or similar lengths that allow for the same or similar stroke lengths for the pistons, but different pump outputs. Such configurations may deliver in series dispensing of a larger volume of either composition 51, 61 by allowing for pistons of different sizes.

Alternatively, the dispenser may be configured to dispense a non-similar ratio (not 1:1) of the first composition 51 to the second composition 61, as shown in FIG. 3A. In some examples, the first pump 90 and second pump 100 may be configured so that the chambers 91, 101 have different lengths and similar or the same diameters. Such configurations may deliver in series dispensing of a larger volume of either composition 51, 61 by allowing for pistons of different stroke lengths.

Alternatively, the first channel 110 and the second channel 120 may be located such that the channels 110, 120 deliver the compositions to an exit orifice 40 located between the exit tubes 92 102, as shown in FIG. 4. Moreover, in contrast to FIG. 2 where the second exit tube 102 is positioned farther away from the exit orifice 40 as compared to the first exit tube 92, the first exit tube 92 and the second exit tube 102 may be positioned so that the first exit tube 92 and the second exit tube 102 are substantially equidistant from the exit orifice 40. As shown in FIG. 4, the first channel 110 and second channel 120 may be configured to deliver their contents to the premix chamber 150 located between the first exit tube 92 and the second exit tube 102. As shown in FIG. 4A, the compositions are delivered to the premix chamber 150 via the first channel 110 and the second channel 120. Once in the premix chamber 150, the mixture of the first and second compositions may travel to the swirl chamber 130 via the first feed 270 and second feed 280. The dispenser may include a separator 391 that assists in forming the first feed 270 and the second feed 280.

Figure 5:
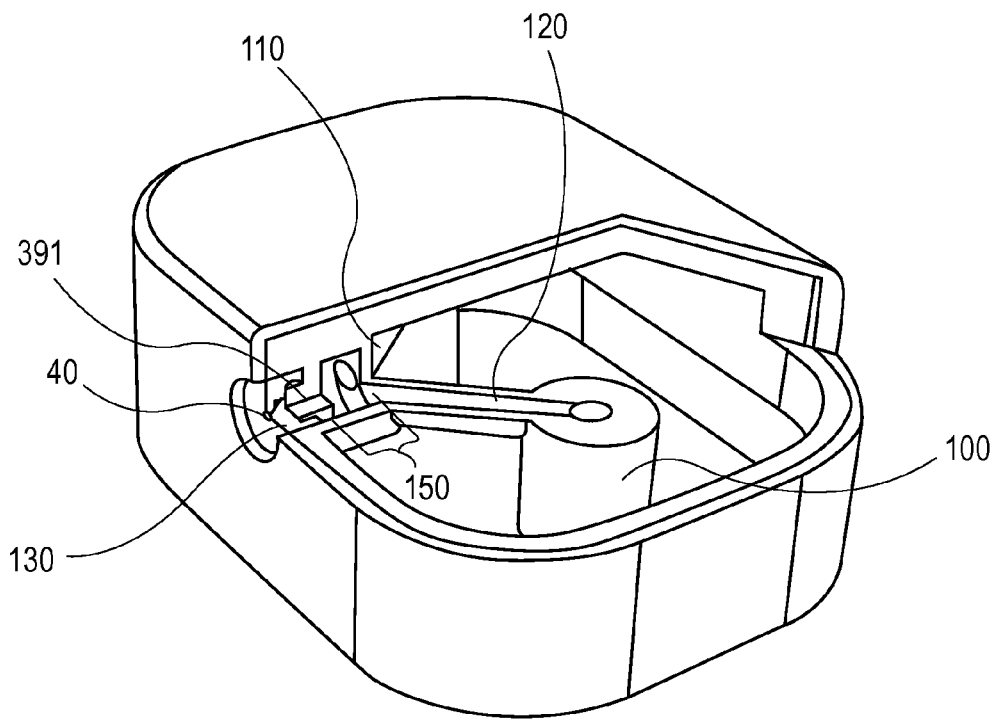
FIG. 5 is a perspective, cross sectional view of the top of a dispenser.
Figure 5A:
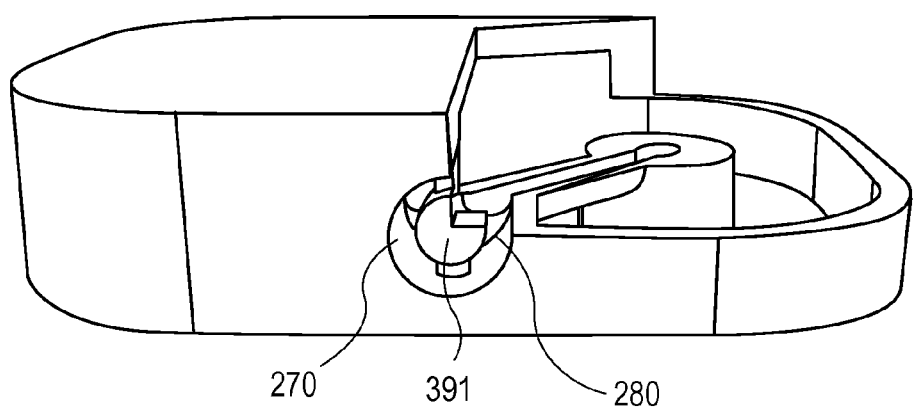
FIG. 5A is a perspective, cross sectional view of top of a dispenser without a swirl chamber.

FIG. 5 shows a three-dimensional cross-section of a configuration for a dispenser where the first channel 110 and the second channel 120 are located such that the channels 110, 120 deliver the compositions to an exit orifice 40 located between the exit tubes 92, 102, similar to the dispenser of FIG. 4. FIG. 5A shows the configuration shown in FIG. 5 without the swirl chamber 130 so that the channels 270, 280 and the separator 391 can be better visualized.

Figure 5B:
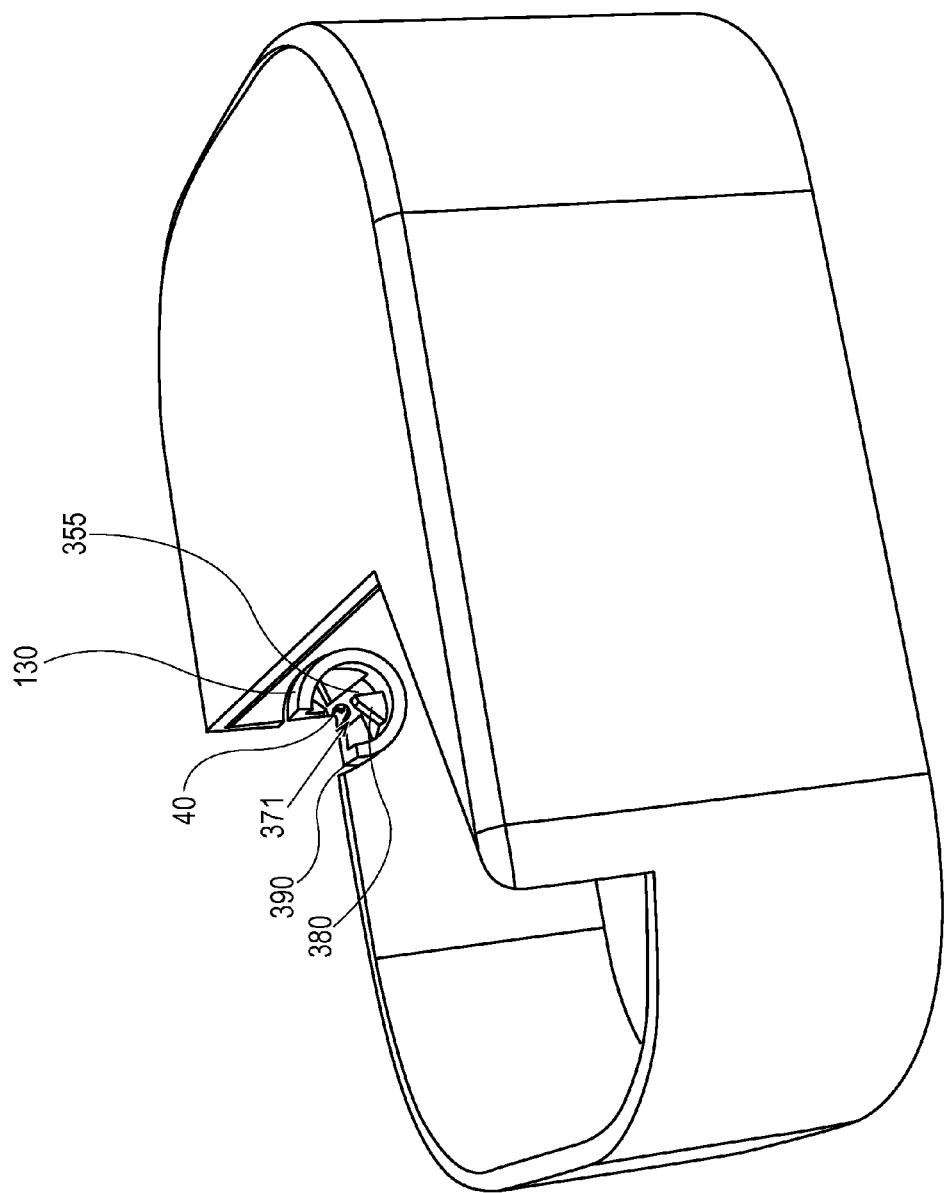
FIG. 5B is a perspective, cross sectional view of a swirl chamber.

FIG. 5B shows a three-dimensional cross-section of a non-limiting example of a swirl chamber 130 that may be included in the dispensers described herein. It is to be noted that the actual design of the swirl chamber may vary and that one of ordinary skill in the art will recognize that many variations in the design of the swirl chamber are possible. The swirl chamber may be used to impart a swirling motion onto the compositions, said swirling motion promoting the atomization of the compositions for delivery via the exit orifice 40 to the external environment.

Referring to FIG. 5B, the swirl chamber 130 may have a wall 390 that forms a cylindrical shape. The swirl chamber 130 may include one or more baffles 380 which help form the flow passages 355. The baffles may be so designed as to form one or more flow passages 355, that serve to deliver their contents to a swirl zone 371. In some examples, the swirl chamber 130 may have at least two flow passages, at least three flow passages, or more than four flow passages. The exit orifice 40 serves to discharge the fluid from the swirl zone 371 to the external environment of the dispenser. In some non-limiting examples, the combined volume of the swirl zone 371 and the flow passages may be from 0.10 cubic millimeters to 1.0 cubic millimeter, such as when the combined volume is 0.21 cubic millimeters.

As shown in FIG. 6, the dispenser may be configured in some examples so that the first channel 110 and the second channel 120 form a concentric arrangement 290 around each other before delivering the compositions into the premix chamber 150. As shown in FIG. 6A, the concentric arrangement 290 may contain an inner concentric channel 292 that contains the contents delivered via the first channel 110 and an outer concentric channel 294 that surrounds the inner concentric channel 292 that delivers the contents of the second channel 120. As shown in FIG. 6B, the compositions are delivered to the premix chamber 150 via the inner concentric channel 292 and the outer concentric channel 294. Once in the premix chamber 150, the mixture of the first and second compositions travels to the swirl chamber 130 via the first feed 270 and second feed 280. The dispenser may include a separator 391 that assists in forming the first feed 270 and the second feed 280. Once in the swirl chamber 130, the mixture of the first and second compositions is released to the external environment via the exit orifice 40.

As shown in FIG. 7, an assembly for flushing 399 may be included to flush the premix chamber 150, swirl chamber 130, and the exit orifice 40 in order to prevent clogging that may result from the residual microcapsules left after each actuation event or to otherwise promote a consistent and seamless actuation experience. Furthermore, the assembly 399 may be used when unequal ratios of the first composition and the second composition are to be dispensed. The assembly 399 may include an actuator 30, a first pump 90, a second pump 100, a first piston 430, and a second piston 440. The first pump 90 and second pump 100 may have a spring 421 biased upwardly against the pistons. The first pump 90 may have a larger output than the second pump 100.

In some examples, the assembly for flushing 399 may be configured to be an assembly 410 that includes an external compensator 450 and a sliding connection 460, as shown in FIG. 7. The external compensator 450 may be made of a flexible/compressible/elastic material and may be a spring as shown. Referring to assembly 410, the force required to move piston 440 is less than the force required to compress the external compensator 450. When the second piston 440 reaches its final position, the external compensator compensates for the shorter distance traveled by the first piston 430 while the sliding connection 460 provides an enclosure capable of receiving the proximal end 570 of the piston rod 558 of the second piston 440 so that the actuator 30 can continue to travel seamlessly. The second piston 440 also has a head 530 at the distal end 575 of the piston rod 558. Thus, the compositions being pumped from the first pump 90 and the second pump 100 are dispensed concurrently followed by only the composition being pumped from the first pump 90. Such a design will flush the premix chamber 150, swirl chamber 130, and the exit orifice 40 with a volume V1 of the composition being pumped by the first pump 90. In such a configuration, the actuator 30 will continue to move in a smooth action while allowing the swirl chamber 130, the premix chamber 150, and the exit orifice 40 to be flushed, providing a seamless actuation experience for the user. It is to be understood that the volume V1 may be adjusted such as by altering the length of strokes of the first piston 430 and second piston 440 and/or by adjusting the diameter of the pumps, accordingly.

Referring to FIG. 8, the assembly 410 may be included in a dispenser 10. In some examples, the second piston 440 of the second pump 100 is in communication with an external compensator 450. The assembly 410 may include a sliding connection 460 (shown as a void space) for receiving the piston rod 558 of the second piston 440 in order to compensate for the difference in distance traveled between the first piston 430 and the second piston 440.

As shown in FIG. 8, the dispenser 10 may be in a first position 403, wherein the first piston 430 and the second piston 440 are in their initial positions and the external compensator 450 is in a relaxed state. As shown in FIG. 8A, the dispenser 10 may be in a second position 404, the second position resulting from the application of force to the actuator 30 by the user, wherein the first piston 430 and the second piston 440 are both operative, leading to the pumping of the first composition 51 and the second composition 61 into the premix chamber 150, swirl chamber 130, and the exit orifice 40, while the external compensator 450 remains in the relaxed state. As shown in FIG. 8B, the dispenser 10 may be in a third position 405, the third position resulting from the continued application of force to the actuator 30 by the user, wherein the first piston 430 is operative and the second piston 440 is in a resting state, leading to the continued pumping of the second composition 61 and cessation of pumping of the first composition 51 into the premix chamber 150, swirl chamber 130, and the exit orifice 40. As shown in FIG. 8C, the dispenser 10 may be in a fourth position 406, the fourth position resulting from the continued application of force to the actuator 30 by the user, wherein the first piston 430 is at its resting state, the second piston 440 remains at a resting state, the external compensator 450 is in a compressed state, and the proximal end 570 of the piston rod 558 of the second piston 440 is located within the sliding connection 460. The fourth position results in the cessation of the pumping of the second composition 61 into the swirl chamber 130 premix chamber 150, and exit orifice 40.

These positions result in two stages of flow for the compositions. In the first stage, the flow of the compositions toward the premix chamber 150 consists of the first composition 51 and the second composition 61 being pumped concurrently until the dispenser 10 enters the third position. Entrance into the third position results in the second stage of flow, at which point the external compensator 450 is compressed, bringing a portion of the piston rod 558 of the second piston 440 into the sliding connection 460 while the first piston 430 continues to travel; leading to a flushing of the premix chamber 150, swirl chamber 130, and the exit orifice 40 with the second composition 61, and a overall seamless actuation experience for the user.

Alternatively as shown in FIG. 9, the assembly for flushing 399 may be configured to be an assembly 411 that includes an internal compensator 550, juxtaposed between the first head 545 and the second head 555 of the second piston 440, to assist in compensating for the shorter distance traveled by the second piston 440 as compared to the first piston 430. The internal compensator 550 may be made of a flexible/compressible/elastic material and may be a spring as shown. The second piston may include a piston rod 558 that is operatively associated with the actuator 30 at the proximal end 570 of the piston rod 558. The second piston is also operatively associated with the first head 545, second head 555, and the internal compensator 550 at the distal end 575 of the piston rod 558. The first head 545 of the second piston 440 may also include an aperture 562 (shown with the piston rod 558 along the inside of the aperture) that allows the piston rod 558 to pass through the first head 545 of the second piston 440 and into a void 560 located within the second pump 100. The void 560 is may receive the piston rod 558 primarily when the first head 545 reaches the stop member 564. The piston rod 558 may also include at least one flange 559 that serves to engage the first head 545, internal compensator 550, and second head 555 for returning said components from the final position to the initial position with the assistance of the force provided by spring 421.

Referring to assembly 411, the force required to move the second piston 440 is less than the force required to compress the internal compensator 550. Assembly 411 provides for a sequence of flow wherein the first and second compositions are pumped simultaneously until the first head 545 of the second piston 440 reaches its final position during actuation, at which point the internal compensator 550 is compressed, bringing the second head 555 in closer proximity to the first head 545. Such a design will flush the premix chamber 150, swirl chamber 130, and the exit orifice 40 with a volume V1 of the composition being pumped by the first pump 90. In such a configuration, the actuator 30 will continue to move in a smooth action despite the premix chamber 150, swirl chamber 130, and the exit orifice 40 being flushed.

Referring to FIG. 10, assembly 411 may be included in a dispenser 10. In such a configuration, engaging the actuator 30 will cause the first piston 430 and the second piston 440 to move, causing the first composition 51 and the second composition 61 to be pumped simultaneously until the first head 545 reaches its final position, at which point the internal compensator 550 is compressed, bringing the first head 545 and the second head 555 in closer proximity as compared to the starting position. When the first head 545 and the second head 555 are in closer proximity, then the second composition 61 will flush the premix chamber 150, swirl chamber 130, and the exit orifice 40, and other components included until the first piston 535 reaches its final position.

When used in a dispenser, assembly 411 may provide the two compositions with two stages of flow. As shown in FIG. 10, the dispenser 10 may be in a first position 403, wherein the first piston 430 and the second piston 440 are in their initial positions with the internal compensator 550 in a relaxed state where neither composition is being pumped into the premix chamber 150, swirl chamber 130, and the exit orifice 40. As shown in FIG. 10A, the dispenser 10 may be in a second position 404, the second position resulting from the application of force to the actuator 30 by the user, wherein the first piston 430 and the second piston 440 are both operative, leading to the pumping of the first composition 51 and the second composition 61 into the premix chamber 150, swirl chamber 130, and the exit orifice 40, while the internal compensator 550 remains in the relaxed state. As shown in FIG. 10B, the dispenser 10 may be in a third position 405, the third position 405 resulting from the continued application of force to the actuator 30 by the user, wherein the first piston 430 is operative and the second piston 440 is in a resting state, leading to the continued pumping of the second composition 61 and cessation of pumping of the first composition 51 into the premix chamber 150, swirl chamber 130, and the exit orifice 40. As shown in FIG. 10C, the dispenser 10 may be in a fourth position 406, the fourth position 406 resulting from the continued application of force to the actuator 30 by the user, wherein the first piston 430 is at its resting state, the second piston 440 remains at a resting state, the internal compensator 550 is in a compressed state, and a portion of the piston rod 558 of second piston 440 is located within a void 560 within the second pump 100. The fourth position 406 results in the cessation of the pumping of the second composition 61 and continued cessation of the pumping of the first composition 51 into the premix chamber 150, the swirl chamber 130, and the exit orifice 40.

These positions result in two stages of flow of the compositions. In the first stage, the flow of the compositions toward the premix chamber 150 consists of the first composition 51 and the second composition 61 being pumped concurrently into the premix chamber 150, swirl chamber 130, and the exit orifice 40 until the dispenser 10 enters the third position 405. Entrance into the third position 405 results in the second stage of flow, at which point the internal compensator 550 will be compressed, bringing the first head 545 and second head 555 in closer proximity and the piston rod 558 into the void 560, pumping the second composition 61 until the first piston 430 reaches its final position, and flushing the premix chamber 150, swirl chamber 130, and the exit orifice 40 with the second composition 61.

As shown in FIG. 11, the assembly for flushing 399 may be configured to be an assembly 412 that includes a pivot point 610 and a pivot hinge 620. The pivot point 610 and pivot hinge 620 compensate for the difference in distance traveled by the first piston 430 and the second piston 440 when the pistons are of different lengths. The actuator 30 is also operatively associated with a first piston 430 and a second piston 440. The first piston 430 is in communication with the first pump 90 and the second piston 440 is in communication with the second pump 100. In some examples, the pivot point 610 is located at an end of the actuator 30 and the pivot hinge 620 is located on the actuator 30 between the first piston 430 and the second piston 440. Assembly 412 allows the actuator 30 to move in a continuous, smooth motion that leads to a flushing of the premix chamber 150, the swirl chamber 130, and the exit orifice 40 by the second composition 61. In some examples, the dispenser may be designed so that the pivot point 610 pivots on the shell of the casing that encases the actuator assembly. In some examples, the pivot point 610 is connected to the shell of the casing by a ball and socket at each end or by a connecting rod that creates a hinge.

The assembly 412 may have a first position 403 when the actuator 30 is not engaged by user. The transition from the first position 403 to the second position 404 results in the first piston 430 and the second piston 440 traveling within the first pump 90 and the second pump 100, respectively. When both the first piston 430 and the second piston 440 are traveling within the first pump 90 and the second pump 100, the first pump 90 and second pump 100 are both productive.

As shown in FIG. 11A, the further application of force 670 may result in a second position 404 wherein said actuator 30 is slanted as compared to the actuator in the first position 403. The presence of the pivot point 610 and pivot hinge 620 allow the second piston 440 to continue traveling in the second pump 100 while allowing for the first piston 430 to remain in its final position. Engaging the actuator 30 so that the assembly 412 enters the second position 405 allows the volume V1 of the second composition 61 to flush the premix chamber 150, the swirl chamber 130, and the exit orifice 40 as the second pump 100 remains productive while the first pump 90 is non-productive. As shown in FIG. 11B, the application of force 670 by the user may alter the position of the apparatus 412 to a third position 405, such that the second piston 440 has now reached its final position within the second pump 100. At position 405, the first pump 90 and the second pump 100 are both non-productive.

Figure 12A:
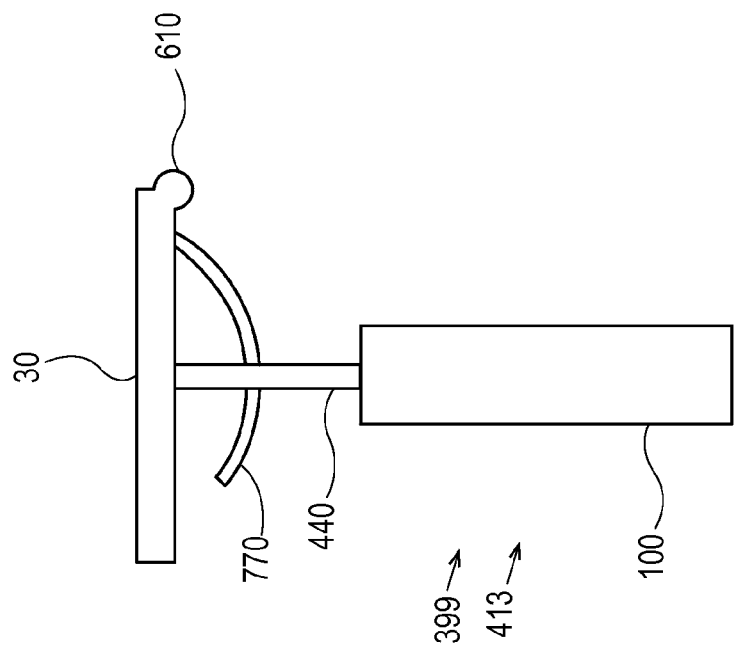
FIG. 12A is a side view of an assembly used in a dispenser.
Figure 12:
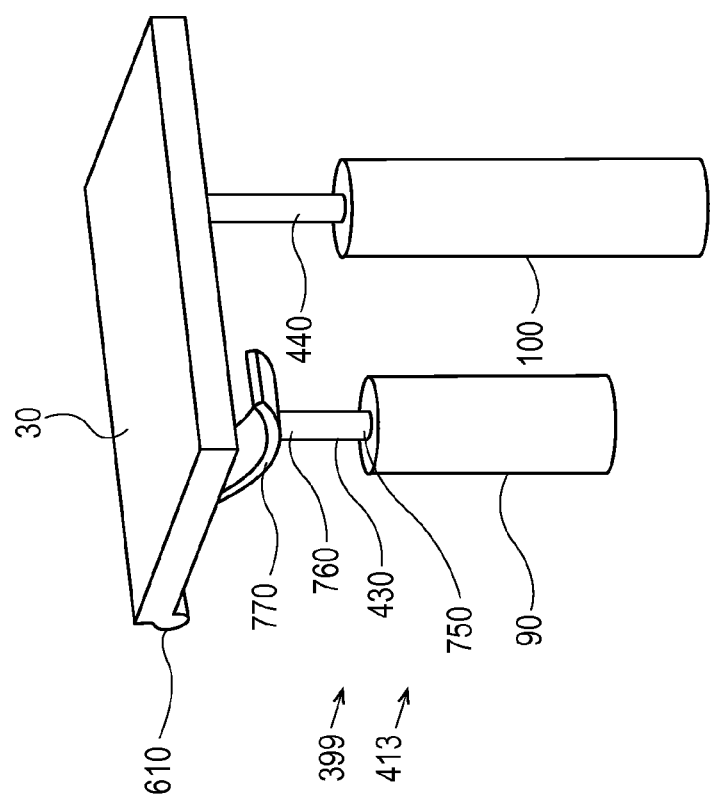
FIG. 12 is a perspective view of an assembly used in a dispenser.

As shown in FIG. 12, an assembly for flushing 399 may be configured to be an assembly 413 that includes a first piston 430 having a first end 750 and a second end 760 wherein the first end 750 of the first piston 430 includes a head 530 (not shown) and the second end 760 of the first piston is operatively associated with an external leaf spring 770. The external leaf spring 770 serves to compensate for the shorter distance traveled by the first piston 430 as compared to the distance traveled by the second piston 440. The second piston 440 is in communication with the second pump 100. The actuator 30 may rotate about the axis provided by a pivot point 610. Alternatively, the assembly 413 may be configured so that it does not include or utilize the pivot point 610 such as by incorporating a compressible external leaf spring 770. The external leaf spring 770 may be positioned in communication with the second pump 100. FIG. 12A shows a side view of assembly 413. As shown in FIG. 13, assembly 413 may be included in a dispenser 10. FIG. 13A shows a side view of a cross-section of assembly 413 when in a dispenser 10. FIG. 13B shows the arrangement of the premix chamber 150, swirl chamber 130, and the exit orifice 40 in relation to the external leaf spring 770.

The incorporation of assembly 413 in dispenser 10 results in two stages of flow for the compositions. FIG. 13C shows assembly 413 in dispenser 10 where the dispenser is in a first position 403. In the first position 403, the first piston 430 and the second piston 440 are in their initial positions. During the first stage, the first composition 51 and second composition 61 flow to the premix chamber 150, swirl chamber 130, and the exit orifice 40 because the first composition 51 and the second composition 61 are pumped concurrently until first piston 430 reaches its final position. The first stage is characterized by a transition of the dispenser from the first position 403 to the second position 404. As shown in FIG. 13D, once the first piston 430 enters its final position, the first pump 90 will no longer be operative until the first and second piston return to their initial positions (see first position 403). If force continues to be applied to the actuator 30 after the first piston 430 reaches its final position, then the actuator 30 will continue to apply force to the second piston 440, allowing the second piston to continue traveling within the second pump 100. The second stage is characterized by the transition of the dispenser from second position 404 to the third position 405. In this regard, the second pump 100 will continue to be operative until the second piston 440 reaches its final position as shown in FIG. 13E. The external leaf spring 770 may be configured to either rotate about an axis (if a pivot point 610 is included) or be compressed (if the pivot point 610 is not included), allowing for a seamless actuation experience by allowing the second pump 100 to be productive while the first pump 90 is no longer productive.

Figure 14A:
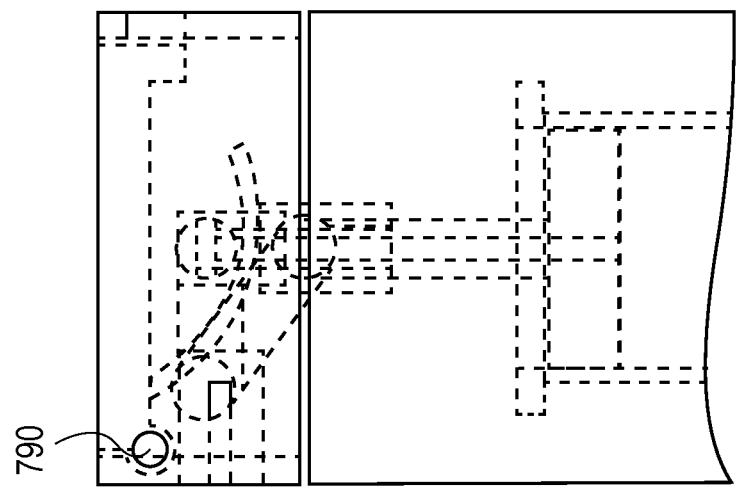
FIG. 14A is a side view of the top of a dispenser.
Figure 14:
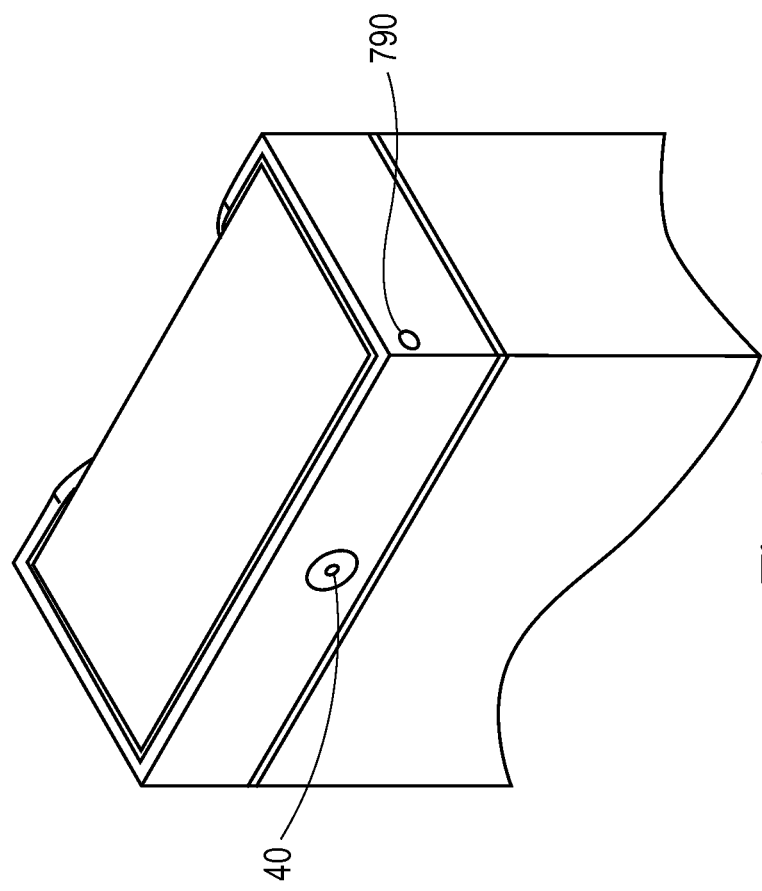
FIG. 14 is a perspective view of the top of a dispenser.

In some examples, the dispenser may be designed so that the pivot point 610 pivots on the shell of the casing that encases the actuator assembly. In some examples, the pivot point 610 is connected to the shell of the casing by a ball and socket at each end. In some examples, the pivot point 610 is connected to the shell by a connecting rod that creates a hinge, as shown in FIG. 14 and FIG. 14A.

Thus, the use of the external leaf spring 770, as shown in FIGS. 13 and 13A-13F, results in two stages of flow of the compositions. In the first stage, the compositions flow toward the premix chamber 150, swirl chamber 130, and the exit orifice 40 until the first piston 430 reaches its final position. During the second stage of flow, the external leaf spring 770 allows the first piston 430 to remain in its final position and allows the second piston 440 to continue traveling within the second pump 100, resulting in a flushing of the premix chamber 150, swirl chamber 130, and the exit orifice 40 with a volume V1 of the second composition 61.

Alternatively, the dispensers may be customized to first mix the two compositions immediately prior to exit by first mixing the compositions within the swirl chamber. As shown in FIG. 15, the dispenser 10 may contain a first reservoir 50 for storing a first composition 51 and a second reservoir 60 for storing a second composition 61. The reservoirs 50, 60 may be of any shape or design. The dispenser may be configured to dispense a similar volume ratio (e.g. 1:1) of the first composition 51 to the second composition 61 as shown in FIG. 15 or configured to dispense a non-similar volume ratio. The first reservoir 50 may have an open end 52 and a closed end 53. The second reservoir may have an open end 62 and a closed end 63. The open ends 52 62 may be used to receive the pump, channel, and/or dip tubes into the reservoirs. The open ends 52 62 may also be used to supply the reservoirs with the compositions. Once supplied, the open ends 52, 62 may be capped or otherwise sealed to prevent leakage from the reservoirs. In some examples, the first composition 51 may include microcapsules 55. The dispenser may include a first dip tube 70 and a second dip tube 80, although the dip tubes are not necessary if alternative means are provided for airless communication between the reservoir and the pump, a non-limiting example of which is a delaminating bottle. The dispenser may include a first pump 90 (shown as a schematic) in communication with the first dip tube 70. The dispenser may also include a second pump 100 (shown as a schematic) in communication with the second dip tube 80. The inner workings of the pumps are routine unless otherwise illustrated in the drawings. Such inner workings have been abbreviated and shown as schematic so as to not obscure the details from the teachings herein. Suitable pumps with outputs between 30 microliters to 140 microliter may be obtained from suppliers such as Aptargroup Inc., MeadWeastavo Corp., and Albea. Some examples of suitable pumps are the pre-compression pumps described in WO2012110744, EP0757592, EP0623060. The first pump 90 may have a chamber 91 and the second pump 100 may have a chamber 101. The pumps as illustrated herein are in some cases magnified to show the inner details and may be smaller in size than they appear as illustrated herein when said pumps are used for a fine fragrance.

The dispenser may include a first channel 110 and a second channel 120. In some non-limiting examples, the channels 110, 120 have a volume of 5 millimeters to 15 millimeters, an example of which is when the channels have a volume of 8.4 cubic millimeters. The first channel 110 may have a proximal end 111 and a distal end 112. The second channel 120 may have a proximal end 121 and a distal end 122. The proximal end 111 of the first channel 110 is in communication with the exit tube 92 of the first pump 90. The proximal end 121 of the second channel 120 is in communication with the exit tube 102 of the second pump 100. The first channel 110 may be of a shorter length as compared to the second channel 120. The second channel 120 may be disposed above the first channel 110 as illustrated in FIG. 3 or below the first channel 110. Alternatively, the first channel and second channel may be substantially coplanar (i.e. exist side-by-side). The exit tubes 92, 102 may have similar or different diameters which can provide for similar or different volumes. In some non-limiting examples, the exit tubes have a diameter of 0.05 millimeters to 3 millimeters, an example of which is when one of the exit tubes has a diameter of 1.4 millimeters and the other exit tube has a diameter of 1 millimeter. In some non-limiting examples, the exit tubes 92, 102 may have a volume of from 2 cubic millimeters to 10 cubic millimeters, such as when one exit tube has a volume of 7.70 cubic millimeters and the other exit tube as a volume of 3.93 cubic millimeters.

The distal end 112 of the first channel 110 and the distal end 122 of the second channel 120 serve to deliver the compositions into the swirl chamber 130. The swirl chamber 130 may impart on the first composition 51 and the second composition 61 a swirl motion. The swirl chamber may be configured to deliver certain spray characteristics. For example, the fluid entering the swirl chamber may be provided a swirling or circular motion or other shape of motion within the swirl chamber, the characteristics of the motion being driven by the inward design of the swirl chamber 130. Incorporation of a swirl chamber 130 may provide sufficient atomization when compositions that vary in surface tension and viscosity are present in the reservoirs. In some instances, the mixing of the two compositions in the swirl chamber may lower the surface tension of the compositions, and thereby, improving the level of atomization of the liquids.

As shown in FIG. 15A, the first channel 110 may have a first diameter 250 and the second channel 120 may have a second diameter 260 such that the first diameter 250 and the second diameter 260 are either the same or about the same. The swirl chamber 130 may include a first feed 270 in communication with the first channel 110 and a second feed 280 in communication with the second channel 120. The first feed 270 may be configured to have about the same diameter as the second feed 280. Alternatively, the first feed 270 and the second feed 280 may have different diameters. Alternatively, the feeds 270, 280 may be of similar or the same diameter. Alternatively, more than one feed may be in communication with each channel. Alternatively more than one feed may be in communication with each channel and each channel may have a disproportionate number of feeds as compared to the other channel. To minimize clogging such as may occur when a composition contains particulates (e.g. microcapsules) or displays a different viscosity from the other composition, the channels 110, 120 may be configured such that one of the channels has a larger diameter than the other.

As shown in FIG. 16, the first channel 110 and second channel 120 may be configured to deliver their contents to the swirl chamber 130 located between the first exit tube 92 and the second exit tube 102. In some examples, the first channel 110 and the second channel 120 may be located such that the channels 110, 120 deliver the compositions to an exit orifice 40 located between the exit tubes 92, 102, as shown in FIG. 16. The first exit tube 92 and the second exit tube 102 may be positioned so that the first exit tube 92 and the second exit tube 102 are substantially equidistant from the swirl chamber 130. FIG. 16A shows a cross-section of a dispenser with the arrangement as shown in FIG. 16 where the first exit tube 92 and the second exit tube 102 deliver the compositions 51, 61 to an exit orifice located between the exit tubes.

As shown in FIG. 17, the dispenser may be configured in some examples so that the first channel 110 and the second channel 120 form a concentric arrangement 290 around each other before delivering the compositions into the swirl chamber 130. As shown in FIG. 17A, the concentric arrangement 290 may contain an inner concentric channel 292 and an outer concentric channel 294 that surrounds the inner concentric channel 292. As shown in FIG. 17B, the concentric arrangement 290 may be configured so that the first channel 110 is in liquid communication with a first feed 270 that delivers the contents from the first channel 110 to the swirl chamber 130. The concentric arrangement 290 may also be configured so that the second channel 120 is in liquid communication with a second feed 280 that delivers the contents from the second channel 120 to the swirl chamber 130.

FIGS. 18-18C show a non-limiting example of a swirl chamber 130 than may be included in the dispenser when the mixing of the compositions is to occur first within the swirl chamber 130. It is to be noted that the actual design of the swirl chamber may vary and that one of ordinary skill in the art will recognize that many variations in the design of the swirl chamber are possible. In some examples, the swirl chamber may be so designed as to mix the contents of the first and second reservoirs within the swirl chamber and immediately prior to exit into the external environment. Moreover, the swirl chamber may be used to impart a swirling motion onto the compositions, said swirling motion promoting the atomization of the compositions for delivery via the exit orifice 40 to the external environment.

Referring to FIG. 18, the swirl chamber 130 may have a wall 390 that forms a cylindrical shape. The swirl chamber 130 may include a first baffle 381, a second baffle 384, a third baffle 386, and a fourth baffle 388 which altogether help form flow passages. The baffles may be so designed as to form a first flow passage 356, a second flow passage 360, a third flow passage 365, and a fourth flow passage 370 that serve to deliver their contents to a mixing zone 371 for mixing just prior to exit via the exit orifice 40. In some examples, the swirl chamber 130 may have at least two flow passages, at least three flow passages, or more than four flow passages. In some non-limiting examples, the combined volume of the mixing zone 371 and the flow passages may be from 0.10 cubic millimeters to 1.0 cubic millimeter, such as when the combined volume is 0.21 cubic millimeters. Referring to FIG. 18A, the swirl chamber 130 may include a separator 391 that forms a first inner swirl channel 392 and a second inner swirl channel 393 for keeping the two compositions separate until delivery to the mixing zone 371. In some non-limiting examples, the combined volume of the first inner swirl channel and the second inner swirl channel may be from 0.05 cubic millimeters to 3.0 cubic millimeter, such as when the combined volume is 1.10 cubic millimeters. The first inner swirl channel 392 may empty its contents into the first flow passage 356 and the second flow passage 360. The second inner swirl channel 393 may empty its contents into the third flow passage 365 and the fourth flow passage 370. As shown in FIG. 18B, the exit orifice 40 serves to discharge the fluid from the mixing zone 371 to the external environment of the dispenser.

Referring to FIG. 19, assembly 410 may be included in a dispenser 10 where the compositions first mix within the swirl chamber 130. The dispenser may include an actuator 30, a swirl chamber 130 in communication with a first channel 110 and a second channel 120. The first channel 110 is also in communication with a first exit tube 92 and the second channel 120 is also in communication with a second exit tube 102. The second piston 440 of the second pump 100 is operatively associated with an external compensator 450. The assembly 410 may include a sliding connection 460 (shown as a void space) for receiving the piston rod 558 of the second piston 440 in order to compensate for the difference in distance traveled between the first piston 430 and the second piston 440. When used in a dispenser 10, assembly 410 may allow for flushing of the swirl chamber 130 and exit orifice 40.

Referring to FIG. 20, assembly 411 may be included in a dispenser 10 where the compositions first mix within the swirl chamber 130. As shown in FIG. 20, the dispenser 10 may include an actuator 30, a swirl chamber 130 in communication with a first channel 110 and a second channel 120. The first channel 110 is also in communication with a first exit tube 92 and the second channel 120 is also in communication with a second exit tube 102. In such a configuration, engaging the actuator 30 will cause the first piston 430 and the second piston 440 to move, causing the first composition 51 and the second composition 61 to be pumped simultaneously until the first head 545 reaches its final position, at which point the internal compensator 550 is compressed, bringing the first head 545 and the second head 555 in closer proximity as compared to the starting position. When the first head 545 and the second head 555 are in closer proximity, then the second composition 61 will flush the swirl chamber 130 and the exit orifice 40 until the first piston 535 reaches its final position.

As shown in FIG. 21, the assembly for flushing 399 may be configured to be an assembly 412 that includes a pivot point 610 and a pivot hinge 620 and used in a dispenser where the compositions first mix within the swirl chamber 130. The pivot point 610 and pivot hinge 620 compensate for the difference in distance traveled by the first piston 430 and the second piston 440 when the pistons are of different stroke lengths. The actuator 30 is also operatively associated with a first piston 430 and a second piston 440. The first piston 430 is in communication with the first pump 90 and the second piston 440 is in communication with the second pump 100. In some examples, the pivot point 610 is located at an end of the actuator 30 and the pivot hinge 620 is located on the actuator 30 between the first piston 430 and the second piston 440. Assembly 412 allows the actuator 30 to move in a continuous, smooth motion that leads to a flushing of the swirl chamber 130 and exit orifice 40 by the second composition 61. In some examples, the dispenser may be designed so that the pivot point 610 is associated with and pivots on the shell of the casing that encases the actuator assembly. In some examples, the pivot point 610 may be connected to the shell of the casing by a ball and socket at each end or by a connecting rod that creates a hinge.

Figure 22:
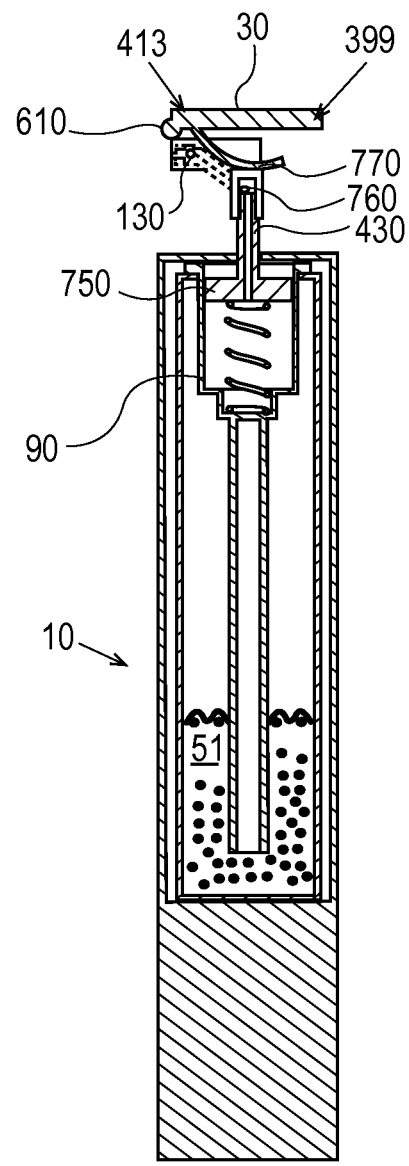
FIG. 22 is a cross sectional, perspective back view of a dispenser.

As shown in FIG. 22, an assembly for flushing 399 may be configured to be an assembly 413 that includes a first piston 430 having a first end 750 and a second end 760 wherein the first end 750 of the first piston 430 is in communication with the first pump 90 and the second end 760 of the first piston is operatively associated with an external leaf spring 770. Assembly 413 may be used in a dispenser where the compositions first mix within the swirl chamber 130. The external leaf spring 770 serves to compensate for the shorter distance traveled by the first piston 430 as compared to the distance traveled by the second piston 440. The second piston 440 is in communication with the second pump 100. The actuator 30 may rotate about the axis provided by a pivot point 610. Alternatively, the assembly 413 may be configured so that it does not include or utilize the pivot point 610. The external leaf spring 770 may be positioned in communication with the second pump 100.

In some examples, the dispensers may incorporate an assembly for flushing 399 for use with compositions that are not described in detail herein when such compositions are incompatible and require storage in separate reservoirs. Thus, the assembly for flushing 399 may be used for particulates not-described herein or for other compositions, a non-limiting example of which is peroxide/oxidation hair dyes, where the flushing is provided by the peroxide.

It is to be understood that minor improvements such as valves to prevent reverse flow are to be included herein without deviating from the inventions herein. A non-limiting example is a valve included to prevent reverse flow from the swirl chamber to the channels. Other non-limiting minor improvements may include a mesh to prevent agglomerated particles from entering the pump.

When the dispenser is used for a fine fragrance application, the dispenser should be configured to dispense the mixture of the first and second compositions with sufficient atomization. Some non-limiting examples of variables that may influence the particle size distribution are the extent of mixing of the first and second compositions, the contents of the compositions themselves, and the inherent design of the dispenser. The particle size distribution may be measured by using a particle size analyzer equipped with laser diffraction technology, such as those that are available from Malvern Instruments (UK).

Table 1 below illustrates a non-limiting example of a suitable particle size distribution for a dispenser providing sufficient atomization for use in a fine fragrance application. Note that for this specific dispenser and composition, the De Brouckere Mean Diameter (i.e. Volume or Mass Moment Mean) (i.e. D[4] [3]) is 98.92 microns and the Sauter Mean Diameter (i.e. Surface Area Moment Mean) (i.e. D[3,2]) is 55.42 microns (see the Technical Paper titled "Basic Principles of Particle Size Analysis" by Dr. Alan Rawle for a description of how to calculate the De Brouckere Mean Diameter and the Sauter Mean Diameter).

Table 1 below illustrates a suitable particle size distribution for a dispenser providing sufficient atomization of a conventional fine fragrance composition:

TABLE 1

| Size ($\mu$M) | % V< | % V |
|---|---|---|
| 0.117 | 0.00 | 0.00 |
| 0.136 | 0.00 | 0.00 |
| 0.158 | 0.00 | 0.00 |
| 0.185 | 0.00 | 0.00 |
| 0.215 | 0.00 | 0.00 |
| 0.251 | 0.00 | 0.00 |
| 0.293 | 0.00 | 0.00 |
| 0.341 | 0.00 | 0.00 |
| 0.398 | 0.00 | 0.00 |
| 0.464 | 0.00 | 0.00 |
| 0.541 | 0.00 | 0.00 |
| 0.631 | 0.00 | 0.00 |
| 0.736 | 0.00 | 0.00 |
| 0.858 | 0.00 | 0.00 |
| 1.00 | 0.00 | 0.00 |
| 1.17 | 0.00 | 0.00 |
| 1.36 | 0.00 | 0.00 |
| 1.58 | 0.00 | 0.00 |
| 1.85 | 0.00 | 0.00 |
| 2.15 | 0.00 | 0.00 |
| 2.51 | 0.00 | 0.00 |
| 2.93 | 0.00 | 0.00 |
| 3.41 | 0.00 | 0.00 |
| 3.98 | 0.00 | 0.00 |
| 4.64 | 0.00 | 0.00 |
| 5.41 | 0.00 | 0.00 |
| 6.31 | 0.00 | 0.00 |
| 7.36 | 0.00 | 0.00 |
| 8.58 | 0.00 | 0.00 |
| 10.00 | 1.26 | 1.26 |
| 11.66 | 1.26 | 0.00 |
| 13.59 | 1.26 | 0.00 |
| 15.85 | 1.26 | 0.00 |

TABLE 1-continued

| Size (μM) | % V< | % V |
|---|---|---|
| 18.48 | 1.28 | 0.03 |
| 21.54 | 1.80 | 0.52 |
| 25.12 | 3.27 | 1.47 |
| 29.29 | 6.18 | 2.91 |
| 34.15 | 10.96 | 4.78 |
| 39.81 | 17.86 | 6.90 |
| 46.42 | 26.80 | 8.94 |
| 54.12 | 37.33 | 10.54 |
| 63.10 | 48.70 | 11.37 |
| 73.56 | 59.96 | 11.26 |
| 85.77 | 70.20 | 10.23 |
| 100.00 | 78.71 | 8.51 |
| 116.59 | 85.13 | 6.43 |
| 135.94 | 89.48 | 4.35 |
| 158.49 | 92.06 | 2.58 |
| 184.79 | 93.35 | 1.28 |
| 215.44 | 93.85 | 0.50 |
| 251.19 | 94.00 | 0.16 |
| 292.87 | 94.13 | 0.13 |
| 341.46 | 94.42 | 0.30 |
| 398.11 | 94.99 | 0.56 |
| 464.16 | 95.82 | 0.83 |
| 541.17 | 96.84 | 1.02 |
| 630.96 | 97.91 | 1.08 |
| 735.64 | 98.89 | 0.97 |
| 857.70 | 99.62 | 0.73 |
| 1000.00 | 100.00 | 0.38 |

The following particle size distribution is possible when a dispenser (10) including a premix chamber (150) and swirl chamber (130), as described herein) sprays a first composition (51) including water and microcapsules (55) and a second composition (51) including a volatile solvent. For such a combination of dispenser and compositions, the De Brouckere Mean Diameter is 91.49 microns and the Satuer Mean Diameter is 71.08 microns. Table 2 below illustrates a suitable particle size distribution for a dispenser providing sufficient atomization for use in a fine fragrance application when the dispenser (10) includes a premix chamber (150) and swirl chamber (130) and is used to spray a first composition (51) including water and microcapsules (55) and a second composition (51) including a volatile solvent:

TABLE 2

| Size (μm) | % V< | % V |
|---|---|---|
| 0.117 | 0.00 | 0.00 |
| 0.136 | 0.00 | 0.00 |
| 0.158 | 0.00 | 0.00 |
| 0.185 | 0.00 | 0.00 |
| 0.215 | 0.00 | 0.00 |
| 0.251 | 0.00 | 0.00 |
| 0.293 | 0.00 | 0.00 |
| 0.341 | 0.00 | 0.00 |
| 0.398 | 0.00 | 0.00 |
| 0.464 | 0.00 | 0.00 |
| 0.541 | 0.00 | 0.00 |
| 0.631 | 0.00 | 0.00 |
| 0.736 | 0.00 | 0.00 |
| 0.858 | 0.00 | 0.00 |
| 1.00 | 0.00 | 0.00 |
| 1.17 | 0.00 | 0.00 |
| 1.36 | 0.00 | 0.00 |
| 1.58 | 0.00 | 0.00 |
| 1.85 | 0.00 | 0.00 |
| 2.15 | 0.00 | 0.00 |
| 2.51 | 0.00 | 0.00 |
| 2.93 | 0.00 | 0.00 |
| 3.41 | 0.00 | 0.00 |
| 3.98 | 0.00 | 0.00 |
| 4.64 | 0.00 | 0.00 |
| 5.41 | 0.00 | 0.00 |
| 6.31 | 0.00 | 0.00 |
| 7.36 | 0.00 | 0.00 |
| 8.58 | 0.00 | 0.00 |
| 10.00 | 0.00 | 0.00 |
| 11.66 | 0.00 | 0.00 |
| 13.59 | 0.00 | 0.00 |
| 15.85 | 0.00 | 0.00 |
| 18.48 | 0.00 | 0.00 |
| 21.54 | 0.00 | 0.00 |
| 25.12 | 0.00 | 0.00 |
| 29.29 | 0.24 | 0.24 |
| 34.15 | 1.46 | 1.22 |
| 39.81 | 4.64 | 3.18 |
| 46.42 | 10.74 | 6.10 |
| 54.12 | 20.30 | 9.56 |
| 63.10 | 33.01 | 12.72 |
| 73.56 | 47.67 | 14.66 |
| 85.77 | 62.43 | 14.75 |
| 100.00 | 75.38 | 12.95 |
| 116.59 | 85.23 | 9.86 |
| 135.94 | 91.62 | 6.39 |
| 158.49 | 95.03 | 3.40 |
| 184.79 | 96.40 | 1.38 |
| 215.44 | 96.73 | 0.33 |
| 251.19 | 96.73 | 0.00 |
| 292.87 | 96.73 | 0.00 |
| 341.46 | 96.73 | 0.00 |
| 398.11 | 96.73 | 0.00 |
| 464.16 | 99.20 | 2.47 |
| 541.17 | 100.00 | 0.80 |
| 630.96 | 100.00 | 0.00 |
| 735.64 | 100.00 | 0.00 |
| 857.70 | 100.00 | 0.00 |
| 1000.00 | 100.00 | 0.00 |

COMPOSITIONS

Volatile Solvents

The compositions described herein may include a volatile solvent or a mixture of volatile solvents. The volatile solvents may comprise greater than 10%, greater than 30%, greater than 40%, greater than 50%, greater than 60%, greater than 70%, or greater than 90%, by weight of the composition. The volatile solvents useful herein may be relatively odorless and safe for use on human skin. Suitable volatile solvents may include $C_1$-$C_4$ alcohols and mixtures thereof. Some non-limiting examples of volatile solvents include ethanol, methanol, propanol, isopropanol, butanol, and mixtures thereof. In some examples, the composition may comprise from 0.01% to 98%, by weight of the composition, of ethanol.

Nonvolatile Solvents

The composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof.

Fragrances

The composition may comprise a fragrance. As used herein, "fragrance" is used to indicate any odoriferous material or a combination of ingredients including at least one odoriferous material. Any fragrance that is cosmetically acceptable may be used in the composition. For example, the fragrance may be one that is a liquid or solid at room temperature. Generally, the non-encapsulated fragrance(s) may be present at a level from about 0.001% to about 40%, from about 0.1% to about 25%, from about 0.25% to about 20%, or from about 0.5% to about 15%, by weight of the composition. Some fragrances can be considered to be volatiles and other fragrances can be considered to be or non-volatiles, as described and defined herein.

A wide variety of chemicals are known as fragrances, non-limiting examples of which include alcohols, aldehydes, ketones, ethers, Schiff bases, nitriles, and esters. More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of about 500° C. or lower, about 400° C. or lower, or about 350° C. or lower. The BP of many fragrances are disclosed in *Perfume and Flavor Chemicals* (Aroma Chemicals), Steffen Arctander (1969). The C log P value of the individual fragrance materials may be about −0.5 or greater. As used herein, "C log P" means the logarithm to the base 10 of the octanol/water partition coefficient. The C log P can be readily calculated from a program called "C LOG P" which is available from Daylight Chemical Information Systems Inc., Irvine Calif., USA or calculated using Advanced Chemistry Development (ACD/Labs) Software V11.02 (© 1994-2014 ACD/Labs). Octanol/water partition coefficients are described in more detail in U.S. Pat. No. 5,578,563.

Examples of suitable aldehyde include but are not limited to: alpha-Amylcinnamaldehyde, Anisic Aldehyde, Decyl Aldehyde, Lauric aldehyde, Methyl n-Nonyl acetaldehyde, Methyl octyl acetaldehyde, Nonylaldehyde, Benzenecarboxaldehyde, Neral, Geranial, 2, 6 octadiene, 1,1 diethoxy-3,7dimethyl-, 4-Isopropylbenzaldehyde, 2,4-Dimethyl-3-cyclohexene-1-carboxaldehyde, alpha-Methyl-p-isopropyldihydrocinnamaldehyde, 3-(3-isopropylphenyl)butanal, alpha-Hexylcinnamaldehyde, 7-Hydroxy-3,7-dimethyloctan-1-al, 2,4-Dimethyl-3-Cyclohexene-1-carboxaldehyde, Octyl Aldehyde, Phenylacetaldehyde, 2,4-Dimethyl-3-Cyclohexene-1-carboxaldehyde, Hexanal, 3,7-Dimethyloctanal, 6,6-Dimethylbicyclo[3.1.1]hept-2-ene-2-butanal, Nonanal, Octanal, 2-Nonenal Undecenal, 2-Methyl-4-(2,6,6-trimethyl-1-cyclohexenyl-1)-2-butenal, 2,6-Dimethyloctanal3-(p-Isopropylphenyl)propionaldehyde, 3-Phenyl-4-pentenal Citronellal, o/p-Ethyl-alpha,alpha-, 9-Decenal, dimethyldihydrocinnamaldehyde, p-Isobutyl-alpha-methyldrocinnamaldehyde, cis-4-Decen-1-al, 2,5-Dimethyl-2-ethenyl-4-hexenal, trans-2-Methyl-2-butenal, 3-Methylnonanal, alpha-Sinensal, 3-Phenylbutanal, 2,2-Dimethyl-3-phenylpropionaldehyde, m-tert.Butyl-alpha-methyldihydrocinnamic aldehyde, Geranyl oxyacetaldehyde, trans-4-Decen-1-al, Methoxycitronellal, and mixtures thereof.

Examples of suitable esters include but are not limited to: Allyl cyclohexanepropionate, Allyl heptanoate, Allyl Amyl Glycolate, Allyl caproate, Amyl acetate (n-Pentyl acetate), Amyl Propionate, Benzyl acetate, Benzyl propionate, Benzyl salicylate, cis-3-Hexenylacetate, Citronellyl acetate, Citronellyl propionate, Cyclohexyl salicylate, Dihydro Isojasmonate Dimethyl benzyl carbinyl acetate, Ethyl acetate, Ethyl acetoacetate, Ethyl Butyrate, Ethyl-2-methyl butryrate, Ethyl-2-methyl pentanoate Fenchyl acetate (1,3,3-Trimethyl-2-norbornanyl acetate), Tricyclodecenyl acetate, Tricyclodecenyl propionate, Geranyl acetate, cis-3-Hexenyl isobutyrate, Hexyl acetate, cis-3-Hexenyl salicylate, n-Hexyl salicylate, Isobornyl acetate, Linalyl acetate, p-t-Butyl Cyclohexyl acetate, (−)-L-Menthyl acetate, o-t-Butylcyclohexyl acetate), Methyl benzoate, Methyl dihydro iso jasmonate, alpha-Methylbenzyl acetate, Methyl salicylate, 2-Phenylethyl acetate, Prenyl acetate, Cedryl acetate, Cyclabute, Phenethyl phenylacetate, Terpinyl formate, Citronellyl anthranilate, Ethyl tricyclo[5.2.1.0-2,6]decane-2-carboxylate, n-Hexyl ethyl acetoacetate, 2-tert.-Butyl-4-methyl-cyclohexyl acetate, Formic acid, 3,5,5-trimethylhexyl ester, Phenethyl crotonate, Cyclogeranyl acetate, Geranyl crotonate, Ethyl geranate, Geranyl isobutyrate, Ethyl 2-nonynoate2,6-Octadienoic acid, 3,7-dimethyl-, methyl ester, Citronellyl valerate, 2-Hexenylcyclopentanone, Cyclohexyl anthranilate, L-Citronellyl tiglate, Butyl tiglate, Pentyl tiglate, Geranyl caprylate, 9-Decenyl acetate, 2-Isopropyl-5-methylhexyl-1 butyrate, n-Pentyl benzoate, 2-Methylbutyl benzoate (mixture with pentyl benzoate), Dimethyl benzyl carbinyl propionate, Dimethyl benzyl carbinyl acetate, trans-2-Hexenyl salicylate, Dimethyl benzyl carbinyl isobutyrate, 3,7-Dimethyloctyl formate, Rhodinyl formate, Rhodinyl isovalerate, Rhodinyl acetate, Rhodinyl butyrate, Rhodinyl propionate, Cyclohexylethyl acetate, Neryl butyrate, Tetrahydrogeranyl butyrate, Myrcenyl acetate, 2,5-Dimethyl-2-ethenylhex-4-enoic acid, methyl ester, 2,4-Dimethylcyclohexane-1-methyl acetate, Ocimenyl acetate, Linalyl isobutyrate, 6-Methyl-5-heptenyl-1 acetate, 4-Methyl-2-pentyl acetate, n-Pentyl 2-methylbutyrate, Propyl acetate, Isopropenyl acetate, Isopropyl acetate, 1-Methylcyclohex-3-enecarboxylic acid, methyl ester, Propyl tiglate, Propyl/isobutyl cyclopent-3-enyl-1-acetate (alpha-vinyl), Butyl 2-furoate, Ethyl 2-pentenoate, (E)-Methyl 3-pentenoate, 3-Methoxy-3-methylbutyl acetate, n-Pentyl crotonate, n-Pentyl isobutyrate, Propyl formate, Furfuryl butyrate, Methyl angelate, Methyl pivalate, Prenyl caproate, Furfuryl propionate, Diethyl malate, Isopropyl 2-methylbutyrate, Dimethyl malonate, Bornyl formate, Styralyl acetate, 1-(2-Furyl)-1-propanone, 1-Citronellyl acetate, 3,7-Dimethyl-1,6-nonadien-3-yl acetate, Neryl crotonate, Dihydromyrcenyl acetate, Tetrahydromyrcenyl acetate, Lavandulyl acetate, 4-Cyclooctenyl isobutyrate, Cyclopentyl isobutyrate, 3-Methyl-3-butenyl acetate, Allyl acetate, Geranyl formate, cis-3-Hexenyl caproate, and mixtures thereof.

Examples of suitable alcohols include but are not limited to: Benzyl alcohol, beta-gamma-Hexenol (2-Hexen-1-ol), Cedrol, Citronellol, Cinnamic alcohol, p-Cresol, Cumic alcohol, Dihydromyrcenol, 3,7-Dimethyl-1-octanol, Dimethyl benzyl carbinol, Eucalyptol, Eugenol, Fenchyl alcohol, Geraniol, Hydratopic alcohol, Isononyl alcohol (3,5,5-Trimethyl-1-hexanol), Linalool, Methyl Chavicol (Estragole), Methyl Eugenol (Eugenyl methyl ether), Nerol, 2-Octanol, Patchouli alcohol, Phenyl Hexanol (3-Methyl-5-phenyl-1-pentanol), Phenethyl alcohol, alpha-Terpineol, Tetrahydrolinalool, Tetrahydromyrcenol, 4-methyl-3decen-5-ol, 1-3,7-Dimethyloctane-1-ol, 2-(Furfuryl-2)-heptanol, 6,8-Dimethyl-2-nonanol, Ethyl norbornyl cyclohexanol, beta-Methyl cyclohexane ethanol, 3,7-Dimethyl-(2),6-octen (adien)-1-ol, trans-2-Undecen-1-ol 2-Ethyl-2-prenyl-3-hexenol, Isobutyl benzyl carbinol, Dimethyl benzyl carbinol, Ocimenol, 3,7-Dimethyl-1,6-nonadien-3-ol (cis & trans), Tetrahydromyrcenol, alpha-Terpineol, 9-Decenol-1, 2 (Hexenyl)cyclopentanol, 2,6-Dimethyl-2-heptanol, 3-Methyl-1-octen-3-ol, 2,6-Dimethyl-5-hepten-2-ol, 3,7,9-Trimethyl-1,6-decadien-3-ol, 3,7-Dimethyl-6-nonen-1-ol, 3,7-Dimethyl-1-octyn-3-ol, 2,6-Dimethyl-1,5,7-octatrienol-3, Dihydromyrcenol, 2,6,10-Trimethyl-5,9-undecadienol, 2,5-Dimethyl-2-propylhex-4-enol-1,(Z),3-Hexenol, o,m,p-Methyl-phenylethanol, 2-Methyl-5-phenyl-1-pentanol, 3-Methylphenethyl alcohol, para-Methyl dimethyl benzyl carbinol, Methyl benzyl carbinol, p-Methylphenylethanol, 3,7-Dimethyl-2-octen-1-ol, 2-Methyl-6-methylene-7-octen-4-ol, and mixtures thereof.

Examples of ketones include but are not limited to: Oxacycloheptadec-10-en-2-one, Benzylacetone, Benzophenone, L-Carvone, cis-Jasmone, 4-(2,6,6-Trimethyl-3-cyclohexen-1-yl)-but-3-en-4-one, Ethyl amyl ketone, alpha-Ionone, Ionone Beta, Ethanone, Octahydro-2,3,8,8-tetramethyl-2-acetonaphthalene, alpha-Irone, 1-(5,5-Dimethyl-1-cyclohexen-1-yl)-4-penten-1-one, 3-Nonanone, Ethyl hexyl ketone, Menthone, 4-Methylacetophenone, gamma-Methyl Ionone Methyl pentyl ketone, Methyl Heptenone (6-Methyl-5-hepten-2-one), Methyl Heptyl ketone, Methyl Hexyl ketone, delta Muscenone, 2-Octanone, 2-Pentyl-3-methyl-2-cyclopenten-1-one, 2-Heptylcyclopentanone, alpha-Methylionone, 3-Methyl-2-(trans-2-pentenyl)-cyclopentenone, Octenyl cyclopentanone, n-Amylcyclopentenone, 6-Hydroxy-3,7-dimethyloctanoic acid lactone, 2-Hydroxy-2-cyclohexen-1-one, 3-Methyl-4-phenyl-3-buten-2-one, 2-Pentyl-2,5,5-trimethylcyclopentanone, 2-Cyclopentylcyclopentanol-1, 5-Methylhexan-2-one, gamma-Dodecalactone, delta-Dodecalactone delta-Dodecalactone, gamma-Nonalactone, delta-Nonalactone, gamma-Octalactone, delta-Undecalactone, gamma-Undecalactone, and mixtures thereof.

Examples of ethers include but are not limited to: p-Cresyl methyl ether, 4,6,6,7,8,8-Hexamethyl-1,3,4,6,7,8-hexahydro-cyclopenta(G)-2-benzopyran, beta-Naphthyl methyl ether, Methyl Iso Butenyl Tetrahydro Pyran, (Phantolide) 5-Acetyl-1,1,2,3,3,6 hexamethylindan, (Tonalid) 7-Acetyl-1,1,3,4,4,6-hexamethyltetralin, 2-Phenylethyl 3-methylbut-2-enyl ether, Ethyl geranyl ether, Phenylethyl isopropyl ether, and mixtures thereof.

Examples of alkenes include but are not limited to: Allo-Ocimene, Camphene, beta-Caryophyllene, Cadinene, Diphenylmethane, d-Limonene, Lymolene, beta-Myrcene, Para-Cymene, alpha-Pinene, beta-Pinene, alpha-Terpinene, gamma-Terpinene, Terpineolene, 7-Methyl-3-methylene-1,6-octadiene, and mixtures thereof.

Examples of nitriles include but are not limited to: 3,7-Dimethyl-6-octenenitrile, 3,7-Dimethyl-2(3), 6-nonadienenitrile, (2E,6Z) 2,6-nonadienenitrile, n-dodecane nitrile, and mixtures thereof.

Examples of Schiffs Bases include but are not limited to: Citronellyl nitrile, Nonanal/methyl anthranilate, Anthranilic acid, N-octylidene-, methyl ester(L)-, Hydroxycitronellal/methyl anthranilate, 2-Methyl-3-(4-Cyclamen aldehyde/methyl anthranilate, methoxyphenyl propanal/Methyl anthranilate, Ethyl p-aminobenzoate/hydroxycitronellal, Citral/methyl anthranilate, 2,4-Dimethylcyclohex-3-enecarbaldehyde methyl anthranilate, Hydroxycitronellal-indole, and mixtures thereof.

Non-limiting examples of fragrances include fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, *eucalyptus* oil, *verbena* oil, *mimosa* extract, *narcissus* extract, carrot seed extract, jasmine extract, olibanum extract, rose extract, and mixtures thereof.

Carriers and Water

When the composition contains microcapsules, the composition may include a carrier for the microcapsules. Non-limiting examples of carriers include water, silicone oils like silicone D5, and other oils like mineral oil, isopropyl myristate, and fragrance oils. The carrier should b e one that does not significantly affect the performance of the microcapsules. Non-limiting examples of non-suitable carriers for the microcapsules include volatile solvents like 95% ethanol.

The compositions containing microcapsules may include about 0.1% to about 95%, from about 5% to about 95%, or from 5% to 75%, by weight of the composition, of the carrier. When the composition contains a volatile solvent, the composition may include from about 0.01% to about 40%, from about 0.1% to about 30%, or from about 0.1% to about 20%, by weight of the composition, of water.

In some examples, when a first composition containing a volatile solvent and a second composition containing microcapsules are sprayed, the dose containing the mixture of the first and second compositions may contain about 0.01% to about 75%, from about 1% to about 60%, from about 0.01% to about 60%, or from about 5% to about 50%, by weight of the composition, of water.

Encapsulates

The compositions herein may include microcapsules. The microcapsules may be any kind of microcapsule disclosed herein or known in the art. The microcapsules may have a shell and a core material encapsulated by the shell. The core material of the microcapsules may include one or more fragrances. The shells of the microcapsules may be made from synthetic polymeric materials or naturally-occurring polymers. Synthetic polymers can be derived from petroleum oil, for example. Non-limiting examples of synthetic polymers include nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and mixtures thereof. Non-limiting examples of suitable shell materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates; acrylate monomers polymerized via free radical polymerization, and mixtures thereof. Natural polymers occur in nature and can often be extracted from natural materials. Non-limiting examples of naturally occurring polymers are silk, wool, gelatin, cellulose, proteins, and combinations thereof.

The microcapsules may be friable microcapsules. A friable microcapsule is configured to release its core material when its shell is ruptured. The rupture can be caused by forces applied to the shell during mechanical interactions. The microcapsules may have a median volume weighted fracture strength of from about 0.1 MPa to about 25.0 MPa, when measured according to the Fracture Strength Test Method, or any incremental value expressed in 0.1 mega Pascals in this range, or any range formed by any of these values for fracture strength. As an example, the microcapsules may have a median volume weighted fracture strength of 0.5-25.0 mega Pascals (MPa), alternatively from 0.5-20.0 mega Pascals (MPa), 0.5-15.0 mega Pascals (MPa), or alternatively from 0.5-10.0 mega Pascals (MPa).

The microcapsules may have a median volume-weighted particle size of from 2 microns to 80 microns, from 10 microns to 30 microns, or from 10 microns to 20 microns, as determined by the Test Method for Determining Median Volume-Weighted Particle Size of Microcapsules described herein.

The microcapsules may have various core material to shell weight ratios. The microcapsules may have a core material to shell ratio that is greater than or equal to: 10% to 90%, 30% to 70%, 50% to 50%, 60% to 40%, 70% to 30%, 75% to 25%, 80% to 20%, 85% to 15%, 90% to 10%, and 95% to 5%.

The microcapsules may have shells made from any material in any size, shape, and configuration known in the art. Some or all of the shells may include a polyacrylate material, such as a polyacrylate random copolymer. For example, the polyacrylate random copolymer can have a total polyacrylate mass, which includes ingredients selected from the group including: amine content of 0.2-2.0% of total polyacrylate mass; carboxylic acid of 0.6-6.0% of total polyacrylate mass; and a combination of amine content of 0.1-1.0% and carboxylic acid of 0.3-3.0% of total polyacrylate mass.

When a microcapsule's shell includes a polyacrylate material, the polyacrylate material may form 5-100% of the overall mass, or any integer value for percentage in this range, or any range formed by any of these values for percentage, of the shell. As examples, the polyacrylate material may form at least 5%, at least 10%, at least 25%, at least 33%, at least 50%, at least 70%, or at least 90% of the overall mass of the shell.

The microcapsules may have various shell thicknesses. The microcapsules may have a shell with an overall thickness of 1-2000 nanometers, or any integer value for nanometers in this range, or any range formed by any of these values for thickness. As a non-limiting example, the microcapsules may have a shell with an overall thickness of 2-1100 nanometers.

The microcapsules may also encapsulate one or more benefit agents. The benefit agent(s) include, but are not limited to, one or more of chromogens, dyes, cooling sensates, warming sensates, fragrances, oils, pigments, in any combination. When the benefit agent includes a fragrance, said fragrance may comprise from about 2% to about 80%, from about 20% to about 70%, from about 30% to about 60% of a perfume raw material with a C log P greater than −0.5, or even from about 0.5 to about 4.5. In some examples, the fragrance encapsulated may have a C log P of less than 4.5, less than 4, or less than 3. In some examples, the microcapsule may be anionic, cationic, zwitterionic, or have a neutral charge. The benefit agents(s) can be in the form of solids and/or liquids. The benefit agent(s) include any kind of fragrance(s) known in the art, in any combination.

The microcapsules may encapsulate an oil soluble material in addition to the benefit agent. Non-limiting examples of the oil soluble material include mono, di- and tri-esters of $C_4$-$C_{24}$ fatty acids and glycerine; isopropryl myristate, soybean oil, hexadecanoic acid, methyl ester, isododecane, and combinations thereof, in addition to the encapsulated benefit agent. The oil soluble material may have a C log P about 4 or greater, at least 4.5 or greater, at least 5 or greater, at least 7 or greater, or at least 11 or greater.

The microcapsule's shell may comprise a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is an aminoalkyl acrylate or aminoalkyl methacrylate.

The microcapsules may include a core material and a shell surrounding the core material, wherein the shell comprises: a plurality of amine monomers selected from the group consisting of aminoalkyl acrylates, alkyl aminoalkyl acrylates, dialkyl aminoalykl acrylates, aminoalkyl methacrylates, alkylamino aminoalkyl methacrylates, dialkyl aminoalykl methacrylates, tertiarybutyl aminethyl methacrylates, diethylaminoethyl methacrylates, dimethylaminoethyl methacrylates, dipropylaminoethyl methacrylates, and mixtures thereof; and a plurality of multifunctional monomers or multifunctional oligomers.

Non-limiting examples of microcapsules include microcapsules that comprise a shell comprising an amine selected from the group consisting of diethylaminoethyl methacrylate, dimethylaminoethyl methacrylate, tertiarybutyl aminoethyl methacrylate; and combinations thereof; a core material encapsulated by said shell, said core material comprising about 10% to about 60% of a material selected from the group consisting of mono, di- and tri-esters of $C_4$-$C_{24}$ fatty acids and glycerine; isopropryl myristate, soybean oil, hexadecanoic acid, methyl ester, isododecane, and combinations thereof, by weight of the microcapsule; and about 10% to about 90% of a perfume material, by weight of the microcapsule; wherein said microcapsules have a volume weighted fracture strength from 0.1 MPa to 25 MPa, preferably from 0.8 MPa to 20 MPa, more preferably from 1.0 MPa to 15 MPa; wherein said microcapsules have a median volume-weighted particle size from 10 microns to 30 microns.

Processes for making microcapsules are well known. Various processes for microencapsulation, and exemplary methods and materials, are set forth in U.S. Pat. No. 6,592,990; U.S. Pat. No. 2,730,456; U.S. Pat. No. 2,800,457; U.S. Pat. No. 2,800,458; U.S. Pat. No. 4,552,811; and U.S. 2006/0263518 A1.

The microcapsule may be spray-dried to form spray-dried microcapsules. The composition may also contain one or more additional delivery systems for providing one or more benefit agents, in addition to the microcapsules. The additional delivery system(s) may differ in kind from the microcapsules. For example, wherein the microcapsule are friable and encapsulate a fragrance, the additional delivery system may be an additional fragrance delivery system, such as a moisture-triggered fragrance delivery system. Non-limiting examples of moisture-triggered fragrance delivery systems include cyclic oligosaccharide, starch (or other polysaccharide material), starch derivatives, and combinations thereof.

The compositions may also include a parent fragrance and one or more encapsulated fragrances that may or may not differ from the parent fragrance. For example, the composition may include a parent fragrance and a non-parent fragrance. A parent fragrance refers to a fragrance that is dispersed throughout the composition and is typically not encapsulated when added to the composition. Herein, a non-parent fragrance refers to a fragrance that differs from a parent fragrance and is encapsulated with an encapsulating material prior to inclusion into a composition. Non-limiting examples of differences between a fragrance and a non-parent fragrance include differences in chemical make-up.

Suspending Agents

The compositions described herein may include one or more suspending agents to suspend the microcapsules and other water-insoluble material dispersed in the composition. The concentration of the suspending agent may range from about 0.01% to about 90%, alternatively from about 0.01% to 15% by weight of the composition.

Non-limiting examples of suspending agents include anionic polymers, cationic polymers, and nonionic polymers. Non-limiting examples of said polymers include vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate and alginic acid, propylene glycol esters, acrylate polymers such as sodium polyacrylate, polyethylacrylate, polyacrylamide, and polyethyleneimine, and inorganic water soluble material such as bentonite, aluminum magnesium silicate, laponite, hectonite, and anhydrous silicic acid. Other suspending agents may include, but are not limited to, Konjac, Gellan, and a methyl vinyl ether/maleic anhydride copolymer crosslinked with decadiene (e.g. Stabileze®).

Other non-limiting examples of suspending agents include cross-linked polyacrylate polymers like Carbomers with the trade names Carbopol® 934, Carbopol® 940, Carbopol® 950, Carbopol® 980, Carbopol® 981, Carbopol® Ultrez 10, Carbopol® Ultrez 20, Carbopol® Ultrez 21, Carbopol® Ultrez 30, Carbopol® ETD2020, Carbopol® ETD2050, Pemulen® TR-1, and Pemulen® TR-2, available from The Lubrizol Corporation; acrylates/steareth-20 methacrylate copolymer with trade name ACRYSOL™ 22 available from Rohm and Hass; acrylates/beheneth-25 methacrylate copolymers, trade names including Aculyn-28 available from Rohm and Hass, and Volarest™ FL available from Croda; nonoxynyl hydroxyethylcellulose with the trade name Amercell™ POLYMER HM-1500 available from Amerchol; methylcellulose with the trade name BENECEL®, hydroxyethyl cellulose with the trade name NATROSOL®; hydroxypropyl cellulose with the trade name KLUCEL®; cetyl hydroxyethyl cellulose with the trade name POLYSURF® 67, supplied by Hercules; ethylene oxide and/or propylene oxide based polymers with the trade names CARBOWAX® PEGs, POLYOX WASRs, and UCON® FLUIDS, all supplied by Amerchol; ammonium acryloyl dimethyltaurate/carboxyethyl-acrylate-crosspolymers like Aristoflex® TAC copolymer, ammonium acryloyl dimethyltaurate/VP copolymers like Aristoflex® AVS copolymer, sodium acryloyl dimethyltaurate/VP crosspolymers like Aristoflex® AVS copolymer, ammonium acryloyl dimethyltaurate/beheneth-25 methacrylate crosspolymers like Aristoflex® BVL or HMB, all available from Clariant Corporation; polyacrylate crosspoylmer-6 with the trade name Sepimax™ Zen, available from Seppic; and cross-linked copolymers of vinyl pyrrolidone and acrylic acid such as UltraThix™ P-100 polymer available from Ashland.

Other non-limiting examples of suspending agents include crystalline suspending agents which can be categorized as acyl derivatives, long chain amine oxides, and mixtures thereof.

Other non-limiting examples of suspending agents include ethylene glycol esters of fatty acids, in some aspects those having from about 16 to about 22 carbon atoms; ethylene glycol stearates, both mono and distearate, in some aspects, the distearate containing less than about 7% of the mono stearate; alkanol amides of fatty acids, having from about 16 to about 22 carbon atoms, or about 16 to 18 carbon atoms, examples of which include stearic monoethanolamide, stearic diethanolamide, stearic monoisopropanolamide and stearic monoethanolamide stearate; long chain acyl derivatives including long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin), a commercial example of which is Thixin® R available from Rheox, Inc. Other non-limiting examples of suspending agents include long chain acyl derivatives, ethylene glycol esters of long chain carboxylic acids, long chain amine oxides, and alkanol amides of long chain carboxylic acids.

Other non-limiting examples of suspending agents include long chain acyl derivatives including N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Non-limiting examples of suitable long chain amine oxides for use as suspending agents include alkyl dimethyl amine oxides (e.g., stearyl dimethyl amine oxide).

Other non-limiting suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Other non-limiting examples of suspending agents include di(hydrogenated tallow) phthalic acid amide, and cross-linked maleic anhydride-methyl vinyl ether copolymer.

Coloring Agents

The compositions herein may include a coloring agent. A coloring agent may be in the form of a pigment. As used herein, the term "pigment" means a solid that reflects light of certain wavelengths while absorbing light of other wavelengths, without providing appreciable luminescence. Useful pigments include, but are not limited to, those which are extended onto inert mineral(s) (e.g., talk, calcium carbonate, clay) or treated with silicone or other coatings (e.g., to prevent pigment particles from re-agglomerating or to change the polarity (hydrophobicity) of the pigment. Pigments may be used to impart opacity and color. Any pigment that is generally recognized as safe (such as those listed in C.T.F.A. cosmetic Ingredient Handbook, $3^{rd}$ Ed., cosmetic and Fragrance Association, Inc., Washington, D.C. (1982), herein incorporated by reference) may be included in the compositions described herein. Non-limiting examples of pigments include body pigment, inorganic white pigment, inorganic colored pigment, pearling agent, and the like. Non-limiting examples of pigments include talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like. The aforementioned pigments can be used independently or in combination.

Other non-limiting examples of pigments include inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Non-limiting examples of pigments include nanocolorants from BASF and multi-layer interference pigments such as Sicopearls from BASF. The pigments may be surface treated to provide added stability of color and ease of formulation. Non-limiting examples of pigments include aluminum, barium or calcium salts or lakes. Some other non-limiting examples of coloring agents include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

A coloring agent may also be a dye. Non-limiting examples include Red 6, Red 21, Brown, Russet and Sienna dyes, Yellow 5, Yellow 6, Red 33, Red 4, Blue 1, Violet 2, and mixtures thereof. Other non-limiting examples of dyes include fluorescent dyes like fluorescein.

Other Ingredients

The compositions may include other ingredients like antioxidants, ultraviolet inhibitors like sunscreen agents and physical sunblocks, cyclodextrins, quenchers, and/or skin care actives. Non-limiting examples of other ingredients include 2-ethylhexyl-p-methoxycinnamate; hexyl 2-[4-(diethylamino)-2-hydroxybenzoyl]benzoate; 4-tert-butyl-4'-methoxy dibenzoylmethane; 2-hydroxy-4-methoxybenzophenone; 2-phenylbenzimidazole-5-sulfonic acid; octocrylene; zinc oxide; titanium dioxide; vitamins like vitamin C, vitamin B, vitamin A, vitamin E, and derivatives thereof; flavones and flavonoids; amino acids like glycine, tyrosine, etc.; carotenoids and carotenes; chelating agents like EDTA, lactates, citrates, and derivatives thereof.

Method of Use

The compositions disclosed herein may be applied to one or more skin surfaces and/or one or more mammalian keratinous tissue surfaces as part of a user's daily routine or regimen. Additionally or alternatively, the compositions herein may be used on an "as needed" basis. The compositions may be applied to any article, such as a textile, or any absorbent article including, but not limited to, feminine hygiene articles, diapers, and adult incontinence articles. For example, while the combinations of the dispensers, assemblies, and compositions described herein are exquisitely designed to be used as a fine fragrance spray, it is understood that such combinations may also be used as a body spray, feminine spray, adult incontinence spray, baby spray, or other spray. The size, shape, and aesthetic design of the dispensers described herein may vary widely.

Test Methods

It is understood that the test methods that are disclosed in the Test Methods Section of the present application should be used to determine the respective values of the parameters of Applicants' invention as such invention is described and claimed herein.

(1) Fracture Strength Test Method

One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in de-ionized (DI) water to form a slurry for characterization. It is to be understood that the fracture strength of microcapsules extracted from a finished product may vary +/−15% from the ranges described herein as the finished product may alter the microcapsules' fracture strength over time.

To calculate the percentage of microcapsules which fall within a claimed range of fracture strengths, three different measurements are made and two resulting graphs are utilized. The three separate measurements are namely: i) the volume-weighted particle size distribution (PSD) of the microcapsules; ii) the diameter of at least 10 individual microcapsules within each of 3 specified size ranges, and; iii) the rupture-force of those same 30 or more individual microcapsules. The two graphs created are namely: a plot of the volume-weighted particle size distribution data collected at i) above; and a plot of the modeled distribution of the relationship between microcapsule diameter and fracture-strength, derived from the data collected at ii) and iii) above. The modelled relationship plot enables the microcapsules within a claimed strength range to be identified as a specific region under the volume-weighted PSD curve, and then calculated as a percentage of the total area under the curve.

a.) The volume-weighted particle size distribution (PSD) of the microcapsules is determined via single-particle optical sensing (SPOS), also called optical particle counting (OPC), using the AccuSizer 780 AD instrument, or equivalent, and the accompanying software CW788 version 1.82 (Particle Sizing Systems, Santa Barbara, Calif., U.S.A.). The instrument is configured with the following conditions and selections: Flow Rate=1 ml/sec; Lower Size Threshold=0.50 µm; Sensor Model Number=LE400-05SE; Autodilution=On; Collection time=120 sec; Number channels=512; Vessel fluid volume=50 ml; Max coincidence=9200. The measurement is initiated by putting the sensor into a cold state by flushing with water until background counts are less than 100. A sample of microcapsules in suspension is introduced, and its density of particles is adjusted with DI water as necessary via autodilution to result in particle counts of at least 9200 per ml. During a time period of 120 seconds the suspension is analyzed. The resulting volume-weighted PSD data are plotted and recorded, and the values of the mean, $10^{th}$ percentile, and $90^{th}$ percentile are determined.

b.) The diameter and the rupture-force value (also known as the bursting-force value) of individual microcapsules are measured via a computer-controlled micromanipulation instrument system which possesses lenses and cameras able to image the microcapsules, and which possesses a fine, flat-ended probe connected to a force-transducer (such as the Model 403A available from Aurora Scientific Inc, Canada, or equivalent), as described in: Zhang, Z. et al. (1999) "Mechanical strength of single microcapsules determined by a novel micromanipulation technique." *J. Microencapsulation*, vol 16, no. 1, pages 117-124, and in: Sun, G. and Zhang, Z. (2001) "Mechanical Properties of Melamine-Formaldehyde microcapsules." *J. Microencapsulation*, vol 18, no. 5, pages 593-602, and as available at the University of Birmingham, Edgbaston, Birmingham, UK.

c.) A drop of the microcapsule suspension is placed onto a glass microscope slide, and dried under ambient conditions for several minutes to remove the water and achieve a sparse, single layer of solitary particles on the dry slide. Adjust the concentration of microcapsules in the suspension as needed to achieve a suitable particle density on the slide. More than one slide preparation may be needed.

d.) The slide is then placed on a sample-holding stage of the micromanipulation instrument. Thirty or more microcapsules on the slide(s) are selected for measurement, such that there are at least ten microcapsules selected within each of three pre-determined size bands. Each size band refers to the diameter of the microcapsules as derived from the Accusizer-generated volume-weighted PSD. The three size bands of particles are: the Mean Diameter +/−2 μm; the $10^{th}$ Percentile Diameter +/−2 μm; and the $90^{th}$ Percentile Diameter +/−2 μm. Microcapsules which appear deflated, leaking or damaged are excluded from the selection process and are not measured.

e.) For each of the 30 selected microcapsules, the diameter of the microcapsule is measured from the image on the micromanipulator and recorded. That same microcapsule is then compressed between two flat surfaces, namely the flat-ended force probe and the glass microscope slide, at a speed of 2 μm per second, until the microcapsule is ruptured. During the compression step, the probe force is continuously measured and recorded by the data acquisition system of the micromanipulation instrument.

f.) The cross-sectional area is calculated for each of the selected microcapsules, using the diameter measured and assuming a spherical particle (πr2, where r is the radius of the particle before compression). The rupture force is determined for each selected particle from the recorded force probe measurements, as demonstrated in Zhang, Z. et al. (1999) "Mechanical strength of single microcapsules determined by a novel micromanipulation technique." *J. Microencapsulation*, vol 16, no. 1, pages 117-124, and in: Sun, G. and Zhang Z. (2001) "Mechanical Properties of Melamine-Formaldehyde microcapsules." *J. Microencapsulation*, vol 18, no. 5, pages 593-602.

g.) The Fracture Strength of each of the 30 or more microcapsules is calculated by dividing the rupture force (in Newtons) by the calculated cross-sectional area of the respective microcapsule.

h.) On a plot of microcapsule diameter versus fracture-strength, a Power Regression trend-line is fit against all 30 or more raw data points, to create a modeled distribution of the relationship between microcapsule diameter and fracture-strength.

i.) The percentage of microcapsules which have a fracture strength value within a specific strength range is determined by viewing the modeled relationship plot to locate where the curve intersects the relevant fracture-strength limits, then reading off the microcapsule size limits corresponding with those strength limits. These microcapsule size limits are then located on the volume-weighted PSD plot and thus identify an area under the PSD curve which corresponds to the portion of microcapsules falling within the specified strength range.

The identified area under the PSD curve is then calculated as a percentage of the total area under the PSD curve. This percentage indicates the percentage of microcapsules falling with the specified range of fracture strengths.

(2) C log P

The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor, and c. A. Ramsden, Eds. P. 295, Pergamon Press, 1990, incorporated herein by reference). C log P values may be calculated by using the "C LOG P" program available from Daylight Chemical Information Systems Inc. of Irvine, Calif. U.S.A. or calculated using Advanced Chemistry Development (ACD/Labs) Software V11.02 (© 1994-2014 ACD/Labs).

(3) Boiling Point

Boiling point is measured by ASTM method D2887-04a, "Standard Test Method for Boiling Range Distribution of Petroleum Fractions by Gas Chromatography," ASTM International.

(4) Volume Weight Fractions

Volume weight fractions are determined via the method of single-particle optical sensing (SPOS), also called optical particle counting (OPC). Volume weight fractions are determined via an AccuSizer 780/AD supplied by Particle Sizing Systems of Santa Barbara Calif., U.S.A. or equivalent.

Procedure:

1) Put the sensor in a cold state by flushing water through the sensor.
2) Confirm background counts are less than 100 (if more than 100, continue the flush).
3) Prepare particle standard: pipette approx. 1 ml of shaken particles into a blender filled with approx. 2 cups of DI water. Blend it. Pipette approx. 1 ml of diluted, blended particles into 50 ml of DI water.
4) Measure particle standard: pipette approx. 1 ml of double diluted standard into Accusizer bulb. Press the start measurement-Autodilution button. Confirm particles counts are more than 9200 by looking in the status bar. If counts are less than 9200, press stop and 10 inject more sample.
5) Immediately after measurement, inject one full pipette of soap (5% Micro 90) into bulb and press the Start Automatic Flush Cycles button.

(5) Test Method for Determining Median Volume-Weighted Particle Size of Microcapsules One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in deionized water to form a capsule slurry for characterization for particle size distribution.

The median volume-weighted particle size of the microcapsules is measured using an Accusizer 780A, made by Particle Sizing Systems, Santa Barbara Calif., or equivalent. The instrument is calibrated from 0 to 300 μm using particle size standards (as available from Duke/Thermo-Fisher-Scientific Inc., Waltham, Mass., USA). Samples for particle size evaluation are prepared by diluting about 1 g of capsule slurry in about 5 g of de-ionized water and further diluting about 1 g of this solution in about 25 g of water. About 1 g of the most dilute sample is added to the Accusizer and the testing initiated using the autodilution feature. The Accusizer should be reading in excess of 9200 counts/second. If the counts are less than 9200 additional sample should be added. Dilute the test sample until 9200 counts/second and then the evaluation should be initiated. After 2 minutes of testing the Accusizer will display the results, including the median volume-weighted particle size.

EXAMPLES

The following examples are given solely for the purpose of illustration and are not to be construed as limiting the invention, as many variations thereof are possible.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

Example 1

Polyacrylate Microcapsule

An oil solution, consisting of 128.4 g Fragrance Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 12.6 microns, a fracture strength of 7.68±2.0 MPa, and a 51%±20% deformation at fracture.

Example 2

Polyacrylate Microcapsules

An oil solution, consisting of 96 g Fragrance Oil, 64 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 12.6 microns, a fracture strength of 2.60±1.2 MPa, 37%±15% deformation at fracture.

Example 3

Polyacrylate Microcapsules

An oil solution, consisting of 128.4 g Fragrance Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1300-1600 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 26.1 microns, a fracture strength of 1.94±1.2 MPa, 30%±14% deformation at fracture.

Example 4

Polyacrylate Microcapsules

An oil solution, consisting of 128.4 g Fragrance Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 2500-2800 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 10.0 microns, a fracture strength of 7.64±2.2 MPa, 56%±20% deformation at fracture.

Example 5

Polyurea/Urethane Microcapsules

An aqueous solution, consisting of 6.06 g Celvol 523 polyvinyl alcohol (Celanese Chemicals) and 193.94 g deionized water, is added into a temperature controlled steel jacketed reactor at room temperature. Then an oil solution, consisting of 75 g Scent A and 25 g Desmodur N3400 (polymeric hexamethylene diisocyanate), is added into the reactor. The mixture is emulsified with a propeller (4 tip, 2" diameter, flat mill blade; 2200 rpm) to desired emulsion droplet size. The resulting emulsion is then mixed with a Z-bar propeller at 450 rpm. An aqueous solution, consisting of 47 g water and 2.68 g tetraethylenepentamine, is added into the emulsion. And it is then heated to 60° C., held at 60° C. for 8 hours, and allowed to cool to room temperature. The median particle size of the resultant microcapsules is 10 microns.

Example 6

Polyurea/Urethane Microcapsules

Prepare the Oil Phase by adding 4.44 grams of isophorone diisocyanate (Sigma Aldrich) to 5.69 grams of Scent A fragrance oil. Prepare a Water Phase by mixing 1.67 grams of Ethylene Diamine (Sigma Aldrich) and 0.04 grams of 1,4-Diazabicyclo[2.2.2]octane (Sigma Aldrich) into 40 grams of a 5 wt % aqueous solution of Polyvinylpyrrolidone K-90 (Sigma Aldrich) at 10 degrees Centigrade. Next, add the Oil Phase contents to 15.0 grams of a 5 wt % aqueous solution of Polyvinylpyrrolidone K-90 (Sigma Aldrich), while agitating the mix at 1400 RPM using a Janke & Kunkel IKA Laboretechnik RW20 DZM motor with a 3-blade turbine agitator for approximately 9 minutes. Next, add the addition of the Water Phase into the emulsified Oil Phase dropwise over a 6.5 minute period, while continuing to agitate at 1400 RPM. Continue to agitate for 23 minutes, then reduce the agitation speed to 1000 RPM. After 3.75 additional hours, reduce the agitation speed to 500 RPM, and continue to agitate for 14 hours. Start heating the dispersion to 50 degrees Centigrade, over a 2 hour period. Age the capsules at 50 C for 2 hours, then collect the microcapsules. The resultant microcapsules have a median particle size of 12 microns.

Example 7

Polyacrylate Microcapsules

The polyacrylate microcapsule with the characteristics displayed in Table 3 may be prepared as follows. An oil solution, consisting of 112.34 g Fragrance Oil, 12.46 g isopropyl myristate, 2.57 g DuPont Vazo-67, 2.06 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.56 grams of tert-butyl amino ethyl methacrylate (Sigma Aldrich), 0.56 grams of beta-carboxy ethyl acrylate (Sigma Aldrich), and 46.23 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

Example 8

Spray Drying of Perfume Microcapsules

The microcapsules of Example 1 are pumped at a rate of 1 kg/hr into a co-current spray dryer (Niro Production Minor, 1.2 meter diameter) and atomized using a centrifugal wheel (100 mm diameter) rotating at 18,000 RPM. Dryer operating conditions are: air flow of 80 kg/hr, an inlet air temperature of 200 degrees Centigrade, an outlet temperature of 100 degrees Centigrade, dryer operating at a pressure of −150 millimeters of water vacuum. The dried powder is collected at the bottom of a cyclone. The collected microcapsules have an approximate particle diameter of 11 microns. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 9

The microcapsules described in EXAMPLES 1-8 may be used as illustrated in the First Composition below at the indicated percentage.

| Second Composition | (% w/w) |
|---|---|
| Ethanol (96%) | 74.88 |
| Fragrance | 14 |
| Water | 10.82 |
| Diethylamino Hydroxybenzol Hexyl Benzoate | 0.195 |
| Ethylhexyl Methoxycinnamate | 0.105 |

| First Composition | (% w/w) |
|---|---|
| Water | 92.5847 |
| Microcapsules | 6.0361 |
| Carbomer | 0.5018 |
| Phenoxyethanol | 0.2509 |
| Magnesium Chloride | 0.2456 |
| Sodium Hydroxide | 0.1254 |
| Disodium EDTA | 0.0836 |

| First Composition | (% w/w) |
|---|---|
| Polyvinyl alcohol | 0.0655 |
| Sodium Benzoate | 0.0409 |
| Potassium Sorbate | 0.0409 |
| Xanthan Gum | 0.0246 |

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for flushing a dispenser, the process comprising:
    combining the dispenser with an assembly for flushing that provides a first stage and a second stage for pumping a first composition from a first reservoir and a second composition from a second reservoir into a swirl chamber and premix chamber;
    wherein during the first stage, the first composition and the second composition are substantially simultaneously pumped from said first and second reservoirs;
    wherein during the second stage, the pumping of the first composition is halted while the pumping of the second composition continues to provide a flushing volume;
    wherein the first stage occurs before the second stage;
    wherein the flushing volume is from about 5 microliters to about 50 microliters; and wherein the dispenser comprises an actuator operatively associated with the first pump and the second pump; and wherein the first composition comprises a carrier that is not a volatile solvent and a plurality of microcapsules and the second composition comprises a volatile solvent.

* * * * *